(12) United States Patent
Hu et al.

(10) Patent No.: US 11,693,008 B2
(45) Date of Patent: Jul. 4, 2023

(54) MATCH-PAIRED MONOCLONAL ANTIBODIES AGAINST MRJP4, ELISA KIT AND COLLOIDAL GOLD IMMUNOASSAY TEST STRIP FOR DETECTING MRJP4

(71) Applicant: Institute of Apicultural Research, Chinese Academy of Agricultural Sciences, Beijing (CN)

(72) Inventors: Han Hu, Beijing (CN); Qiaohong Wei, Beijing (CN); Si Chen, Wuhan (CN); Mao Feng, Beijing (CN); Lifeng Meng, Beijing (CN); Bin Han, Beijing (CN); Yu Fang, Beijing (CN); Chuan Ma, Beijing (CN); Jianke Li, Beijing (CN)

(73) Assignee: Institute of Apicultural Research, Chinese Academy of Agricultural Sciences, Beijing (CN)

( * ) Notice: Subject to any disclaimer, the term of this patent is extended or adjusted under 35 U.S.C. 154(b) by 632 days.

(21) Appl. No.: 16/774,078

(22) Filed: Jan. 28, 2020

(65) Prior Publication Data
US 2020/0292547 A1    Sep. 17, 2020

(30) Foreign Application Priority Data

Mar. 15, 2019    (CN) .......................... 201910196297.6

(51) Int. Cl.
| | | |
|---|---|---|
| *G01N 33/577* | (2006.01) | |
| *C07K 16/18* | (2006.01) | |
| *G01N 33/53* | (2006.01) | |
| *G01N 33/535* | (2006.01) | |

(52) U.S. Cl.
CPC ........... *G01N 33/577* (2013.01); *C07K 16/18* (2013.01); *G01N 33/5302* (2013.01); *G01N 33/535* (2013.01)

(58) Field of Classification Search
CPC ............. G01N 33/577; G01N 33/5302; G01N 33/535; G01N 33/558
See application file for complete search history.

(56) References Cited

U.S. PATENT DOCUMENTS 7,297,554 B2 * 11/2007 Chung ................. G01N 33/558
436/523

FOREIGN PATENT DOCUMENTS

| CN | 101206226 B | * 10/2012 | |
| WO | WO-2018191422 A1 | * 10/2018 | ............. A23L 21/00 |

OTHER PUBLICATIONS

Bo Yeon Kim, Kwang Sik Lee, Boknam Jung, Yong Soo Choi, Hye Kyung Kim, Hyung Joo Yoon, Zhong-Zheng Gui, Jungkwan Lee, Byung Rae Jin, "Honeybee (*Apis cerana*) major royal jelly protein 4 exhibits antimicrobial activity", 2019, Journal of Asia-Pacific Entomology, vol. 22, Issue 1, pp. 175-182 (Year: 2019).*

* cited by examiner

*Primary Examiner* — Bao-Thuy L Nguyen
*Assistant Examiner* — Alexander Alexandrovic Volkov
(74) *Attorney, Agent, or Firm* — Bayramoglu Law Offices LLC

(57) ABSTRACT

Match-paired monoclonal antibodies against major royal jelly protein 4 (MRJP4) are secreted by hybridoma cell lines having microbial deposit numbers of CGMCC No. 17294 and CGMCC No. 17295, which are used in an ELISA kit and a colloidal gold immunoassay strip for detecting the MRJP4. The positive and MRJP4-specific cell lines are obtained by cell fusion using an antigen of MRJP4 recombinant protein and a cross-reaction with other major royal jelly proteins. The MRJP4 recombinant protein is used as an antigen to obtain several positive cell lines by cell fusion and two MRJP4-specific fusion cell lines are obtained by a cross-reaction with other major royal jelly proteins. Primary screening of a matched antibody pair is performed according to antibody pairing for recognizing different epitopes.

11 Claims, 7 Drawing Sheets
Specification includes a Sequence Listing.

Negative: C line showed color, T line did not show color within 10 minutes, which was negative.

Positive: C line showed color, T line visible to the naked eye within 10 minutes, no matter the color depth is judged to be positive.

Invalid: C line does not show color, whether T line does or not, the detection card is judged to be invalid.

Negative: C line showed color, T line did not show color within 10 minutes, which was negative.
Positive: C line showed color, T line visible to the naked eye within 10 minutes, no matter the color depth is judged to be positive.
Invalid: C line does not show color, whether T line does or not, the detection card is judged to be invalid.

MATCH-PAIRED MONOCLONAL ANTIBODIES AGAINST MRJP4, ELISA KIT AND COLLOIDAL GOLD IMMUNOASSAY TEST STRIP FOR DETECTING MRJP4

CROSS REFERENCE TO THE RELATED APPLICATIONS

This application is based upon and claims priority to Chinese Patent Application No. 201910196297.6, filed on Mar. 15, 2019, the entire contents of which are incorporated herein by reference.

TECHNICAL FIELD

The present invention relates to a preparation and an application of a monoclonal antibodies against major royal jelly protein 4 (MRJP4). In particular, the present invention further relates to a construction of an enzyme-linked immunosorbent assay (ELISA) kit and a colloidal gold immunoassay test strip using a match-paired monoclonal antibodies for detecting MRJP4 and application in the field of qualitative and quantitative detections of MRJP4.

BACKGROUND

Royal jelly is one of the natural functional bee products having the functions of nourishing the health and prolonging life. Royal jelly has complex ingredients, is rich in nutrients, and contains a protein content of 12.0% to 15.0%. Since royal jelly is difficult to preserve and extremely perishable, the quality of royal jelly is closely related to the freshness of the royal jelly. Currently, there is a lack of an internationally accepted method that can be widely used to accurately reflect the freshness of royal jelly.

China is the first producer and exporter of royal jelly in the world. Therefore, it is imperative to explore and establish a method to evaluate the freshness of the royal jelly. Studies have shown that the major royal jelly proteins are positively correlated with the freshness of royal jelly. That is, the fresher the royal jelly, the higher the content of the major royal jelly proteins. MRJP4 is very sensitive to the storage temperature and its concentration gradually decreases over time in the conditions of cold storage or at room temperature.

The MRJP4 antigen is used in a cell fusion method to select a matched-paired antibodies with high specificity and sensitivity. The matched monoclonal antibody pair is further used to construct an ELISA kit and a colloidal gold immunoassay test strip. The ELISA kit can realize the absolute quantification of MRJP4 and the colloidal gold immunoassay test strip can quickly, on-site, detect the MRJP4 content in a few minutes, which provides a reliable and practical method for detecting the freshness of royal jelly.

SUMMARY

The first objective of the present invention is to provide a matched MRJP4 monoclonal antibody pair with good specificity and high sensitivity against the MRJP4 protein.

The second objective of the present invention is to apply the prepared matched MRJP4 monoclonal antibody pair to a qualitative or quantitative detection of the MRJP4.

The third objective of the present invention is to provide an enzyme-linked immunosorbent assay (ELISA) kit for quantitatively detecting the content of the MRJP4 in a test sample.

The fourth objective of the present invention is to provide a colloidal gold immunoassay test strip for qualitatively detecting whether or not a test sample contains the MRJP4.

The objectives of the present invention are realized by the following technical solutions.

In the present invention, the entire/whole sequence of the MRJP4 was subjected to a transmembrane domain analysis, a signal peptide analysis, a hydrophobicity analysis, a chaotic sequence analysis, an antigenicity analysis, a homology analysis, and a structural domain analysis. The amino acid sequence of SEQ ID No: 1 was finally selected as an antigen sequence which was expressed in $E.\ coli$ to prepare an antigen. In the present invention, the prepared antigen was further used to immunize Balb/c mice after being purified and fused cells were prepared by a cell fusion technique. The fused cells were cultured in a semi-solid media and a liquid media to obtain a total of 12 plates of cells and a total of 64 positive cell lines were obtained. Twenty of the 64 positive cell lines were selected for a first subcloning and after a detection of the first subclones, 14 cell lines were selected for a second subcloning followed by three rounds of subcloning. After detecting a cross reaction between the cell lines and the recombinant proteins of other major royal jelly proteins and a cross reaction between the cell lines and natural proteins of other major royal jelly proteins, the cell lines where the cross reaction occurred were removed. Finally 9 MRJP4-specific fusion cell lines were obtained, five cell lines of which with the highest affinity were selected for a subsequent experiment of antibody pairing for recognizing different epitopes. The subsequent preliminary screening of match-paired antibodies was performed according to the results of the antibody pairing for recognizing different epitopes. Finally, according to the results of the antibody pairing for recognizing different epitopes, a standard curve drawing, and a sample test, it was found that the match-paired antibodies of 6H92B8 (hereinafter referred to as 6H9) and 8C93B10 (hereinafter referred to as 8C9) have a relatively good linear relationship and high sensitivity. Therefore, 6H9 and 8C9 were used to construct the ELISA kit and the colloidal gold immunoassay test strip for detecting the MRJP4.

In the present invention, the hybridoma cell lines secreting 6H9 and 8C9 were submitted to a depositary institution designated by the State Intellectual Property Office for preservation, wherein the hybridoma cell line secreting the monoclonal antibody 6H9 has a microbial deposit number of CGMCC No. 17294. The classification and nomenclature is a mouse hybridoma cell. The depository authority is China General Microbiological Culture Collection Center (CGMCC). The deposit date was is Feb. 18, 2019. The deposit address is No. 3, No. 1 Yard, Beichen West Road, Chaoyang District, Beijing, China.tell The hybridoma cell line secreting the monoclonal antibody 8C9 has a microbial deposit number of CGMCC No. 17295. The classification and nomenclature is a mouse hybridoma cell. The depository authority is CGMCC. The deposit date was Feb. 18, 2019. The deposit address is No. 3, No. 1 Yard, Beichen West Road, Chaoyang District, Beijing, China.

An enzyme-linked immunosorbent assay kit for quantitatively detecting the MRJP4 by an ELISA method is further provided in the present invention and includes a primary antibody against the MRJP4, a biotin-labeled secondary antibody against the MRJP4, a standard, a horseradish peroxidase (HRP)-labeled avidin, a biotin-labeled antibody diluent, a HRP-labeled avidin diluent, a sample diluent, a concentrated washing solution, a substrate solution, and a stop solution. The primary antibody is the monoclonal antibody 6H9 against the MRJP4 and the secondary antibody is the monoclonal antibody 8C9 against the MRJP4. Alternatively, the primary antibody is the monoclonal antibody 8C9 against the MRJP4 and the secondary antibody is the monoclonal antibody 6H9 against the MRJP4.

A working principle or a method of detecting a content of the MRJP4 by the kit provided in the present invention is as follows: coating a microplate with a purified primary antibody against the MRJP4 to prepare a solid phase carrier and sequentially adding a sample or the standard, the biotin-labeled secondary antibody against the MRJP4, and the HRP-labeled avidin into a microwell of the microplate coated with the antibody against the MRJP4, and after thorough washing, using tetramethylbenzidine (TMB) as a substrate for a color development. TMB turns blue under a catalysis of a peroxidase and finally turns yellow under an action of an acid. A color depth is positively correlated with the MRJP4 in the sample. An absorbance (optical density) (OD) value is measured at a wavelength of 450 nm using a microplate reader to calculate a concentration of the sample.

The result of the quantitative determination of the MRJP4 content in the sample by the double antibody sandwich ELISA using the enzyme-linked immunosorbent assay kit of the present invention showed that the enzyme-linked immunosorbent assay kit had a detection range of 1.563 ng/mL-100 ng/mL and a detection sensitivity of 3.758 ng/mL.

A colloidal gold immunoassay test strip for rapidly qualitatively detecting the MRJP4 is further provided in the present invention and includes a gold colloidal pad, a nitrocellulose (NC) membrane containing a detecting line and a quality controlling line, a sample pad, a water absorbing pad and a detecting bottom plate. The NC membrane includes one detecting line and one quality controlling line. The detecting line is composed of the monoclonal antibody 6H9 and 8C9 and the quality controlling line is composed of a goat anti-mouse immunoglobulin G (IgG) antibody.

The gold colloidal conjugate pad and the NC membrane containing the detecting line and the quality controlling line may be prepared according to conventional preparation methods of colloidal gold immunoassay kits.

For reference, a method for preparing a gold colloidal conjugate pad is provided in the present invention, including:

(1) conjugating a colloidal gold solution with the monoclonal antibody 6H9 and 8C9 to obtain a colloidal gold-antibody conjugate stock solution; and (2) diluting the colloidal gold-antibody conjugate stock solution and then uniformly adding onto a glass fiber membrane and drying to obtain the gold colloidal conjugate pad.

Various parameters in the method of preparing the gold colloidal conjugate pad and the NC membrane containing the detecting line and the quality controlling line are further optimized in the present invention. Through optimization experiments, it was found that the following preparation methods can effectively improve the detection effect.

In the present invention, through a colloidal gold gradient method, it is found that an optimal conjugate effect was obtained when the monoclonal antibody 6H9 or 8C9 is conjugated with the colloidal gold solution at a pH of 7.4.

In the present invention, through a protein gradient method, it was found that the minimum amount of the monoclonal antibody 6H9 or 8C9 required for stabilizing 1 mL of the colloidal gold is 10 μg/mL.

Test results showed that when a working concentration of the colloidal gold-antibody conjugate stock solution is 1:4 dilution, the obtained gold colloidal conjugate pad has the best detection effect.

Further, in preparing the NC membrane containing the detecting line (T line) and the quality controlling line (C line), a plurality of concentration gradients of coating antibodies on the T line and the C line of the NC membrane are further set for test in the present invention. The results showed that a set of antibodies having the optimal color development effect are as follows: the monoclonal antibody 6H9 or 8C9 on the T line with an optimal working concentration of 2 mg/mL and the goat anti-mouse IgG antibody (on the C line) with an optimal working concentration of 1 mg/mL.

In the present invention, a method for applying the colloidal gold immunoassay test strip for qualitatively detecting whether or not a sample contains the MRJP4 is further includes:

(1) adding the sample to a sample well on a sample pad of the kit; and (2) if the sample is positive, a purple-red band appears in a T zone after adding the sample. If the sample is negative, no purple-red band appears in the T zone and a purple-red band appears in a C zone regardless of a presence of the MRJP4 protein in the sample.

The colloidal gold immunoassay test strip for detecting the MRJP4 provided in the present invention has the characteristics of convenience, rapidity and sensitivity, and is suitable for large-scale sample detection on site. The result of quantitatively determining the content of the MRJP4 in the sample by using the enzyme-linked immunosorbent assay kit provided in the present invention indicates that the detection range of the enzyme-linked immunosorbent assay kit in the present invention is 1.563 ng/mL-100 ng/mL and the detection sensitivity is 3.758 ng/mL. The results of the specificity experiments show that the enzyme-linked immunosorbent assay kit and the colloidal gold immunoassay test strip in the present invention can be used for performing a specific detection on the MRJP4 and avoids a cross reaction with other related proteins (MRJP1, MRJP2, MRJP3, and MRJP5).

DETAILED DESCRIPTION OF THE EMBODIMENTS

Figure 1:
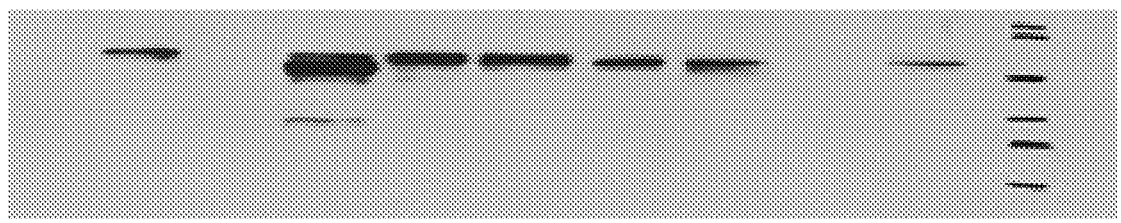
FIG. 1 shows detection results of western blotting for subtypes of 9 cell lines that stably secrete positive antibodies and do not have a cross reaction with MRJP1, MRJP2, MRJP3 and MRJP5.
Figure 1:
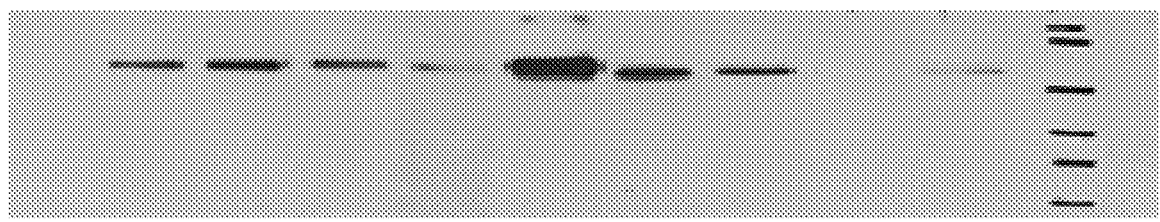

The present invention is further described in combination with the specific embodiments and the advantages and features of the present invention will become clearer with the below description. However, it should be understood that the embodiments are merely illustrative and are not intended to limit the scope of the present invention. It should also be understood by those skilled in the art that the details and forms of the present invention may be modified or substituted without departing from the spirit and scope of the present invention and such modifications or substitutions still fall within the scope of the present invention.

Embodiment 1 Preparation of MRJP4 Monoclonal Antibody and Antibody Pairing

I. Sequence Analysis of MRJP 4 Gene and Selection of Antigen Sequence

The MRJP 4 gene encodes a protein having an amino acid sequence of 464 amino acids and has no transmembrane domain. A sequence of amino acid residues 1-21 of the amino acid sequence is a probable signal peptide sequence. The protein has relatively good hydrophilicity on the whole and the amino acid sequence is different from that of other homologous proteins in the MRJPs family.

A transmembrane domain analysis, a signal peptide analysis, a hydrophobicity analysis, a chaotic sequence analysis, an antigenicity analysis, a homology analysis, and a structural domain analysis were performed and the amino acid sequence of SEQ ID No. 1 was finally selected as an antigen sequence which was expressed in *E. coli* to prepare an antigen.

II. Preparation and Purification of Antigen

1. Small-Scale Expression 1.1 A correct recombinant plasmid identified by sequencing was transformed into an expression host.

1.2 An individual bacterial colony containing the recombinant plasmid was selected into 3 mL of Lysogeny broth (LB) medium (containing antibiotics) and incubated overnight at 37° C.

1.3 30 μL of the overnight culture solution was added into another 3 mL of the LB medium and vibrated and incubated at 37° C. until OD600 of the culture solution was about 0.6. The remaining overnight culture solution was added with glycerin to obtain a seed solution containing 20% glycerin and the seed solution was stored at −80° C. for subsequent use in work.

1.4 A portion of the seed solution was taken as an uninduced control group and an isopropyl-β-D-thiogalactopyranoside (IPTG) inducer was added into the remaining seed solution to obtain a final concentration of 0.5 mM, which was used as an experimental group. The two groups were further vibrated and cultured at 37° C. for 3 hours.

1.5 1 mL of each bacterial solution was centrifuged at 12000×g for 30 s to obtain a precipitate and the precipitate was resuspended with 100 μL of 1% sodium dodecyl sulfate (SDS), then uniformly mixed and placed at 100° C. for 10 min, centrifuged at 12000×g for 10 min and then a supernatant was obtained for SD S-PAGE analysis.

2. Protein Expression and Cell Disruption Detection 2.1 20 μL of the strain stored at −80° C. was transferred into 20 mL of liquid LB medium (containing a corresponding antibiotic).

2.2 2 mL of an overnight culture solution was added into 2000 mL of LB medium, and vibrated and cultivated at 37° C. until the OD600 was about 0.6 and then the temperature was reduced to 30° C.

2.3 The IPTG inducer was added to a final concentration of 0.5 mM as the experimental group and continuously shaken and cultured for 3 hours at 30° C.

2.4 A fermentation broth was collected and centrifuged at 6000×g for 10 min to obtain strains. The strains were suspended in 40 mL of pre-cooled NTA-0 buffer.

2.5 A ultrasonic treatment was performed to disrupt the bacterial cells in an ice bath, wherein the power was controlled to be 300 W and the ultrasonic treatment was performed for 4 s and paused for 4 s, for 90 times.

2.6 A centrifugation was performed at 20000×g at 4° C. for 30 min to obtain a supernatant and a precipitate.

2.7 Small amount of the supernatant was selected for SDS-PAGE detection. The remaining supernatant and precipitate were stored at 0° C.-7° C. for subsequent use.

After the detection of SDS-PAGE, the purification of antigen MRJP4 from *E. coli* was expanded to a concentration of 2 mg/mL, a molecular weight of 38 Kd, and a purity of 80%.

3. Protein Purification 3.1 A suitable chromatographic column was packed with Ni-NTA and 10 column bed volumes of NTA-0 buffer was used for washing.

3.2 The supernatant was added into the chromatographic column with a flow rate of about 0.5 mL/min and the part passing through the chromatographic column was collected.

3.3 The chromatography was realized by using 10 column bed volumes of the NTA-0 buffer for washing at a flow rate of about 1 mL/min.

3.4 10 column bed volumes of NTA-20 buffer, NTA-60 buffer, NTA-200 buffer, and NTA-500 buffer were respectively used for elution (Note: the NTA-20, NTA-60, NTA-200, and NTA-500 buffers are NTA-0 buffers containing 20 mmol/L of imidazole, 60 mmol/L of imidazole, 200 mmol/L of imidazole, and 500 mmol/L of imidazole, respectively) at a flow rate of about 1 mL/min and then each elution peak was collected.

3.5 SDS-PAGE was used to detect the various components.

3.6 The component, whose purity meets the requirements, was dialyzed in 1×phosphate buffered saline (PBS) solution at 4° C. (the solution was changed twice).

3.7 The dialysis product was concentrated by ultrafiltration at 4° C.

III. Preparation of Antibody

1. Immunization of Mice and Evaluation of Serum Titer 1.1 Adult female Balb/c mice at the age of 8 weeks were selected for immunization. The antigen was mixed with an equal volume of a complete adjuvant (first immunization) and an incomplete adjuvant (booster immunization) for emulsification, after uniformly mixing to a water-in-oil state, multiple-site subcutaneous immunizations and 2-3 times of booster immunizations were carried out. The titer was detected after each immunization interval of 2 weeks. An antigen at an immunization dose directly dissolved in PBS was intraperitoneally administered within 1 week for a final booster immunization after the titer greater than 1:50000 was detected. The specific immunization procedure is shown in Table 1.

TABLE 1

Immunization Procedures in Mice

| Times of Immunization | Preparation of Immunogen | Route of Immunization | Period of Immunization | Dose of Immunization (Mice) |
|---|---|---|---|---|
| First immunization | Antigen + Freund's complete adjuvant + PBS | Subcutaneous (or intradermal) | 2-3 weeks | 50-100 μg/mouse |
| Second immunization | Antigen + Freund's incomplete adjuvant + PBS | Subcutaneous (or intradermal) | 2 weeks | 50-80 μg/mouse |
| Third immunization | Antigen + Freund's incomplete adjuvant + PBS | Subcutaneous (or intradermal) | 2 weeks | 50-80 μg/mouse |
| Titer detection | If the titer is relatively low, continue to perform the fourth immunization. | | 1 week | |
| Fourth immunization | Antigen + Freund's incomplete adjuvant + PBS | Subcutaneous (or intradermal) | 1 week | 50-80 μg/mouse |
| Titer detection | 7 days after the fourth immunization, if the titer is greater than 1:12800, then the cell fusion can be performed. | | | |
| Final booster immunization | Antigen + PBS | Intraperitoneal | 3 days before the cell fusion | 50-100 μg/mouse |

1.2 Titer detection method after immunization: an indirect method was used to detect the serum titer. The specific method was as follows:

1.2.1 Coating: a 96-well plate was coated with 1 μg/mL of the antigen at 50 μL/well and placed at 37° C. for 2 h or 4° C. overnight.

1.2.2 Blocking: 2% bovine serum albumin (BSA) or 5% skimmed milk blocking solution was added at 200 μL/well and then the plate was placed at 37° C. for 1 hour or 4° C. overnight and then the plate was washed with TBST 4 times.

1.2.3 Primary antibody: antiserum was added for doubling dilution by using a sample diluent at 1:1000, 1:2000, 1:4000, 1:8000, 1:16000, 1:32000, 1:64000, 1:128000.

1.2.4 After incubating at 37° C. for 1 hour, the plate was washed 4 times and added with a secondary antibody solution at 100 μL/well and then incubated for 1 hour at 37° C., wherein the secondary antibody solution was obtained by diluting a secondary antibody from Jackson ImmunoResearch at 1:10000 with an enzyme diluent.

1.2.5 Color development after the plate was washed 4 times: a substrate solution was added at 100 μL/well and the plate was placed in an incubator at 37° C. for 5-10 min.

1.2.6 Stop reaction and colorimetric assay: a stop solution was added at 30 μL/well and the color turned yellow. The absorbance at 450 nm was measured with a microplate reader.

1.3. Results of Serum Titer

The results of the titer detection are shown in Table 2.

TABLE 2

Results of serum titer detection

| dilution | 1-left | 1-right | 1-middle | 1-nothing | 2-left | 2-right | 2-middle | 2-nothing | Blank blood |
|---|---|---|---|---|---|---|---|---|---|
| Antiserum titer after the third immunization with E-MRJP4 protein 2015 Jun. 22 | | | | | | | | | |
| 1/1000 | 2.7311 | 2.9909 | 2.8325 | 2.856 | 2.981 | 2.856 | 2.8325 | 3.2662 | 0.3045 |
| 1/2000 | 2.6592 | 2.953 | 2.758 | 2.6977 | 2.886 | 2.7488 | 2.7966 | 3.0321 | 0.1088 |
| 1/4000 | 2.6467 | 2.8027 | 2.7082 | 2.9085 | 2.8027 | 2.7912 | 2.9085 | 3.2918 | 0.0952 |
| 1/8000 | 2.7585 | 2.8302 | 2.9589 | 2.8531 | 2.7681 | 2.8531 | 2.9741 | 3.1203 | 0.095 |
| 1/16000 | 2.7819 | 2.837 | 2.837 | 2.7239 | 2.837 | 2.8867 | 2.837 | 3.2912 | 0.0399 |
| 1/32000 | 2.438 | 2.7804 | 2.6835 | 2.7592 | 2.6582 | 2.6749 | 2.7293 | 3.0023 | 0.0242 |
| 1/64000 | 2.0077 | 2.4377 | 2.4713 | 2.1855 | 2.3734 | 2.3577 | 2.3655 | 2.6948 | 0.0076 |
| 1/128000 | 1.2849 | 2.0094 | 2.1806 | 1.5955 | 1.5993 | 1.9036 | 2.0281 | 2.4623 | 0.012 |
| Antiserum titer after the fourth immunization with E-MRJP4 protein 2015 Jul. 6 | | | | | | | | | |
| 1/1000 | 2.835 | 2.8443 | 2.8943 | 2.835 | 3.1453 | 2.916 | 3.0599 | 2.8366 | 0.254 |
| 1/2000 | 2.6964 | 2.7657 | 2.8584 | 2.9502 | 2.9376 | 2.9502 | 2.8482 | 2.9124 | 0.883 |
| 1/4000 | 2.7976 | 2.8283 | 2.7878 | 2.8178 | 3.0261 | 2.8613 | 3.0431 | 2.9992 | 0.3678 |
| 1/8000 | 2.7034 | 2.8075 | 2.7034 | 2.8655 | 2.8553 | 2.876 | 2.8453 | 3.1467 | 0.0801 |
| 1/16000 | 2.5778 | 2.6528 | 2.7674 | 2.8014 | 2.8014 | 2.8582 | 2.8788 | 3.0167 | 0.0963 |
| 1/32000 | 2.5072 | 2.6615 | 2.6189 | 2.5749 | 2.7381 | 2.7381 | 2.7232 | 2.9619 | 0.0437 |
| 1/64000 | 2.3246 | 2.5952 | 2.5054 | 2.4474 | 2.5249 | 2.6319 | 2.5506 | 2.5236 | 0.0306 |
| 1/128000 | 1.8411 | 2.4785 | 2.2799 | 1.9458 | 2.2455 | 2.3142 | 2.2455 | 2.0905 | 0.04 |

The results of the titer detection showed that the serum titer of the mice after immunization was good and the sensitivity was relatively high, which fully meets the requirements of subsequent experiments.

2. Cell Fusion

Three days after the final booster immunization, the mice were sacrificed by removing the eyes for collecting blood as the positive control. The spleen of each mouse was taken out to prepare a single cell suspension. Subsequently, the SP2/0 cells in the logarithmic phase were selected for treatment and then mixed with the splenocytes in a certain ratio (1:5-1:10). 50% PEG1450 was added for acting 1 min, which was terminated by diluting with the Dulbecco's modified Eagle's medium (DMEM). After a low-speed centrifugation, HAT medium containing 20% fetal bovine serum was added for gent suspension, then uniform mixing was performed to obtain a cell suspension, which was distributed to pre-prepared plates for feeder layer cells according to $2 \times 10^7$ cells/plate and cultured in an incubator with 5% $CO_2$ at 37° C. The specific steps are shown as follows:

2.1 Splenocytes: an immuned spleen was removed from a mouse after dissection and separated to yield the lymphocytes in the spleen.

2.1.1 One 1.5 mL centrifuge tube added with 1 mL of serum-free medium, two 3.5 cm culture dishes added with 2 mL of the serum-free medium, two 15 mL centrifuge tubes with one added with 10 mL of the serum-free medium, surgical instruments (sterilized at high pressure and moist heat), tulle netting, pipette (1 mL), and pipette tips were prepared in a clean bench.

2.1.2. The immunized BALB/c mouse was selected for removing the eyes and collecting blood and the serum was isolated as the positive control serum for antibody detection. Meanwhile, the mouse was sacrificed by cervical dislocation, soaked in 75% alcohol for 5 min, and fixed on a wax plate for cutting the skin of the spleen. The spleen was taken out with forceps and placed in a 1.5 mL centrifuge tube.

2.1.3 The spleen was transferred to one of the 3.5 cm culture dishes in the clean bench. The adipose tissue and connective tissue on the surface of the spleen were removed and the spleen was washed one time. A piece of the tulle netting was spread over the lid of the culture dish. The spleen was gently squeezed and placed in the middle of the tulle netting. The tulle netting was folded twice in half. The lymphocytes of the spleen were gently blown by the pipette absorbing the serum-free medium and ground with a grinding rod for passing through the tulle netting to obtain a single cell suspension. The single cell suspension was collected in the 15 mL centrifuge tube and centrifuged at 1000 rpm for 5 min.

2.2 Preparation of SP2/0 cells: a tumor was isolated to prepare a single cell suspension, which was centrifuged at 1000 rpm for 5 min for discarding supernatant. The tumor cells were resuspended with 10-20 mL of DMEM (depending on the size of the tumor) and mixed evenly. The tumor cells were separated by using a lymphocyte separating medium. The lymphocyte separating medium was slowly added dropwise to the resuspended tumor cells in a volume ratio of the lymphocyte separating medium to DMEM of 1:1, followed by centrifuging at 2500 rpm for 15 min and then carefully placed on the clean bench. The milky white halo in the middle layer was transferred to a new centrifuge tube (30 mL of DMEM was pre-prepared in the centrifuge tube) with the pipette, followed by centrifuging at 1000 rpm for 5 min. Finally, the supernatant was discarded and the cells were collected in a 10 cm culture dish. 10% fetal bovine serum was used for adjusting state and expanding culture. In general, the tumor of one mouse can be prepared into 3-5 dishes on the same day and expanded to 30 dishes by centrifugation on the next day and then 30-35 tubes can be cryopreserved.

When preparing for fusion, the following steps were performed:

(a) performing a recovery of cells on the first day;

(b) passaging the cells on the next day according to the number of the fusions, 5 dishes/1 fusion; and (c) observing the state of the cells after about two days. If the logarithmic phase is reached, then collecting the cells for fusion.

2.3 Preparation of feeder layer cells: the spleen of a healthy Balb/c mouse was taken out under sterile conditions and prepared into a single spleen cell suspension with the HAT medium supplemented with 20% fetal bovine serum. Then, the single spleen cell suspension was distributed on a 96-well plate according to the number of plates.

2.4 Stop solution: 20 mL of base medium DMEM was put in a 37° C. water bath for incubation.

3. Construction of Cell Line 3.1. Detection of Fusion Plates

The cells on the fusion plate after a medium change were detected (the detection method is ELISA) when grown to a medium size and with a number of more than 10,000 cells/well. After the quality control of the ELISA was qualified (i.e., negative control<0.2, positive control>1.0), the positive wells (generally OD450≥0.5) were selected for subcloning.

3.1.1 Detection method: the titer was detected by indirect ELISA.

3.1.1.1 Antigen coating: the antigen was diluted to 2 µg/mL with a coating solution added to a 96-well polystyrene reaction plate at 100 µL/well and placed at 4° C. overnight.

3.1.1.2 Washing: on the next day, the liquid in the wells was discarded and the wells were washed with a washing solution three times.

3.1.1.3 Blocking: a blocking solution was added at 150 µL/well and placed at room temperature for 0.5 hours.

3.1.1.4 Washing: the wells were washed with a washing solution three times.

3.1.1.5 Addition of the sample to be tested (primary antibody): antiserum (the blood was taken and placed at 4° C. overnight and then centrifuged at 1000 r/min for 10 min to obtain the supernatant) was added. The antiserum was doubling diluted at 1:200, 1:400, 1:800, 1:1600, 1:3200, 1:6400, and 1:12800 using a sample diluent (serum blank was used as a negative control) and the diluted antiserum was added at 100 µL/well and incubated for 1 hour.

3.1.1.6 Washing: the wells were washed with the washing solution three times.

3.1.1.7 Addition of enzyme-labeled anti-antibody: the wells were added with HRP-labeled goat anti-mouse IgG (1:5000, diluted with an enzyme diluent) at 100 µL/well and incubated for 40 min at 37° C.

3.1.1.8 Washing: the wells were washed five times with the washing solution and two times with distilled water.

3.1.1.9 Color development: the wells were added with a freshly prepared substrate solution at 100 µL/well and placed in dark at room temperature for 5-30 min.

3.1.1.10 Stop reaction and colorimetric assay: the wells were added with the stop solution at 50 µL/well. The solution turned yellow and the absorbance of each well was measured with a microplate reader at 450 nm.

3.2 Detection Result of Cell Fusion

Fusions of a total of 12 plates of cells were performed in the semi-solid medium and liquid medium, and a total of 64 positive cell lines were obtained, wherein 50 of the 64 positive cell lines had titer value OD greater than 2.0 and 14 of the 64 positive cell lines had OD ranging from 1.0 to 2.0.

4. Subcloning Method and Detection

From the above results, the wells with high positive values in the fusion plate were selected for limiting dilution. Subcloning was performed on 60% of the number of monoclonal wells per plate. Each time, a monoclonal well with a relatively high positive value was selected for limiting dilution. The ELISA assay was performed 5 to 7 days after subcloning, until the monoclonal cell line stably secreted the positive antibody was finally screened out for expanded culturing.

4.1 Detection of the First Subcloning

The results of the first subcloning are shown in Table 3.

TABLE 3

First subcloning results

| 6B9 | | 7F1 | | 6H9 | |
|---|---|---|---|---|---|
| 3.2574 | 3.1531 | 0.8742 | 0.6329 | 4.1196 | 3.3543 |
| 3.3515 | 3.5564 | 0.6592 | 0.663 | 3.2071 | 3.1772 |
| 3.1373 | 4.438 | 0.8577 | 0.5778 | 3.1393 | 4.4504 |
| 3.2103 | 3.3699 | 1.0686 | 0.5717 | 2.9476 | 3.0926 |
| 3.4961 | 3.2408 | 0.8999 | 0.5122 | 2.9852 | 3.8049 |
| 3.388 | 3.1687 | 0.6606 | 0.6514 | 2.9688 | 2.9848 |
| 3.2203 | 3.1857 | 0.3816 | 0.5255 | 3.1438 | 2.9164 |
| 3.2935 | 3.6248 | 0.1925 | 0.6236 | 3.6497 | 3.6607 |

| 6D2 | | 6F4 | | 6E2 | |
|---|---|---|---|---|---|
| 3.1836 | 3.1241 | 3.5389 | 3.0579 | 3.1798 | 3.3236 |
| 2.7916 | 3.1185 | 4.4716 | 3.1736 | 3.1473 | 3.5675 |
| 3.0712 | 3.2488 | 3.271 | 3.2429 | 3.3 | 3.1657 |
| 2.9658 | 3.0766 | 3.0351 | 3.3092 | 3.1551 | 3.7546 |
| 3.2656 | 3.1103 | 2.975 | 3.1523 | 3.1208 | 4.3995 |
| 3.1802 | 3.0255 | 3.1614 | 3.297 | 3.1859 | 3.5317 |
| 3.0001 | 3.3816 | 3.7641 | 3.3816 | 4.4585 | 3.7535 |
| 3.3486 | 3.1541 | 3.5336 | 3.1577 | 3.2721 | 3.4193 |

| 8F6 | | 4H5 | | 8C9 | |
|---|---|---|---|---|---|
| 2.0884 | 0.786 | 3.1881 | 3.2632 | 4.419 | 3.7224 |
| 1.5754 | 2.4758 | 3.1645 | 3.2808 | 3.4576 | 3.7605 |
| 2.7998 | 1.6542 | 29207 | 2.9769 | 2.9769 | 3.388 |
| 1.5278 | 0.4186 | 2.726 | 2.7999 | 3.0433 | 3.4357 |
| 0.7121 | 2.5341 | 2.9418 | 2.894 | 3.1629 | 3.1825 |
| 2.9061 | 0.7721 | 2.83 | 3.4683 | 3.3083 | 3.059 |
| 0.7826 | 0.8453 | 2.9125 | 3.2909 | 2.9724 | 3.4339 |
| 0.8554 | 0.3428 | 2.7125 | 3.1228 | 2.8418 | 3.2859 |

| 7G8 | | 12A1 | | 6C12 | |
|---|---|---|---|---|---|
| 2.6584 | 2.2281 | 0.037 | 0.0169 | 2.319 | 2.0466 |
| 1.9399 | 3.2836 | 0.0432 | 0.7283 | 2.9993 | 2.2451 |
| 1.9186 | 0.5431 | 0.6276 | 0.0227 | 1.7122 | 3.0218 |
| 1.4672 | 2.4404 | 0.4152 | 0.6586 | 1.8012 | 2.4533 |
| 2.3289 | 3.1009 | 0.0163 | 0.0471 | 3.1755 | 2.0139 |
| 2.7645 | 2.9871 | 0.1279 | 0.1886 | 0.6009 | 1.5524 |
| 1.2381 | 2.993 | 0.0135 | 0.0309 | 2.5496 | 2.7721 |
| 2.6695 | 2.9719 | 0.1104 | 0.0683 | 2.6384 | 1.2967 |

| 10H6 | | 5G10 | |
|---|---|---|---|
| 0.0065 | 0.0099 | 2.8645 | 4.4298 |
| 0.0084 | 0.0441 | 1.639 | 0.4947 |
| 0.3105 | 0.021 | 0.7846 | 2.9473 |
| 0.0091 | 0.0052 | 2.5172 | 1.2211 |
| 0.0051 | 0.4117 | 3.3349 | 1.646 |
| 0.0103 | 0.0087 | 3.1892 | 0.48 |
| 0.0076 | 0.0065 | 0.5654 | 3.1822 |
| 0.0352 | 0.1905 | 0.6704 | 3.8311 |

Detection method: indirect ELISA.
Primary antibody: first subclone supernatant.
Secondary antibody: goat anti-mouse IgG 1:10000.
Detection time: 2015. 11. 2.
Coated recombinant protein: 1 μg/mL.

4.2 Detection of the Second Subcloning

The results of the second subcloning are shown in Table 4.

TABLE 4

Second subcloning results

| 6B9 | | 7F1 | | 6H9 | |
|---|---|---|---|---|---|
| 0.0466 | 3.2838 | 2.4782 | 2.6686 | 2.7774 | 2.939 |
| 0.2451 | 0.0884 | 0.6425 | 2.591 | 2.7296 | 3.0946 |
| 3.0218 | 1.3946 | 2.4412 | 1.481 | 2.6675 | 2.6149 |
| 2.4533 | 0.4658 | 2.342 | 2.4064 | 2.5337 | 2.6189 |
| 2.0139 | 1.2188 | 2.531 | 0.8986 | 2.5131 | 2.6946 |
| 0.5524 | 2.7753 | 2.3746 | 3.3261 | 2.4993 | 2.4885 |
| 2.7721 | 2.8246 | 2.2521 | 0.802 | 2.5237 | 2.559 |
| 1.2967 | 0.794 | 1.7294 | 2.3544 | 2.3316 | 2.4288 |

| 6D2 | | 6F4 | | 6E2 | |
|---|---|---|---|---|---|
| 2.6654 | 2.6943 | 2.801 | 0.781 | 0.0127 | 4.4269 |
| 2.8415 | 1.863 | 2.7957 | 3.1417 | 2.9201 | 0.0207 |
| 2.7634 | 2.2441 | 2.9158 | 2.925 | 1.3118 | 2.4451 |
| 2.7598 | 2.6389 | 2.5581 | 2.7533 | 3.6535 | 3.5967 |
| 2.688 | 2.6899 | 2.8557 | 0.4672 | 0.0273 | 0.0688 |
| 2.5077 | 2.7801 | 2.5942 | 0.6632 | 3.8211 | 3.0038 |
| 2.659 | 2.6867 | 2.6639 | 2.6034 | 1.0093 | 1.6104 |
| 2.216 | 1.5563 | 2.5287 | 2.5041 | 3.381 | 0.0578 |

| 8F6 | | 4H5 | | 8C9 | |
|---|---|---|---|---|---|
| 0.0561 | 0.0387 | 3.9663 | 3.4367 | 4.4313 | 3.4349 |
| 0.0314 | 0.0302 | 3.173 | 4.162 | 3.3003 | 3.2932 |
| 0.0309 | 0.0409 | 3.2768 | 3.339 | 3.7547 | 3.414 |
| 0.033 | 0.0932 | 3.2493 | 3.2266 | 3.2564 | 3.0762 |
| 0.6852 | 0.0317 | 2.88 | 3.1935 | 30582 | 3.0251 |
| 0.0389 | 0.0358 | 2.9088 | 2.9487 | 2.9337 | 3.044 |
| 0.0352 | 0.0351 | 3.0317 | 3.3156 | 3.2563 | 3.1139 |
| 0.709 | 0.0498 | 2.904 | 3.3573 | 3.1849 | 3.1625 |

| 7G8 | | 12A1 | | 6C12 | |
|---|---|---|---|---|---|
| 3.8189 | 0.3041 | 0.0127 | 4.4269 | 3.8189 | 0.3041 |
| 3.4625 | 0.8739 | 2.9201 | 0.0207 | 3.4625 | 0.8739 |
| 3.2901 | 2.8669 | 1.3118 | 2.4451 | 3.2901 | 2.8669 |
| 3.0416 | 0.2605 | 3.6535 | 3.5967 | 3.0416 | 0.2605 |
| 2.9634 | 0.0185 | 0.0273 | 0.0688 | 2.9634 | 0.0185 |
| 0.989 | 2.6903 | 3.8211 | 3.0038 | 0.989 | 2.6903 |
| 0.3685 | 0.0194 | 1.0093 | 1.6104 | 0.3685 | 0.0194 |
| 2.884 | 0.0341 | 3.381 | 0.0578 | 2.884 | 0.0341 |

| 10H6 | | 5G10 | |
|---|---|---|---|
| 4.4167 | 3.2657 | 0.0343 | 0.0392 |
| 3.2117 | 0.0176 | 0.0261 | 0.0274 |
| 0.0238 | 4.4316 | 0.1817 | 0.0425 |
| 1.2016 | 3.0765 | 0.0279 | 0.0399 |
| 1.8624 | 0.0201 | 0.1879 | 0.0268 |
| 0.0279 | 0.0187 | 0.0362 | 0.0478 |
| 0.0307 | 0.7303 | 0.0321 | 0.0395 |
| 2.9664 | 1.1215 | 0.0385 | 0.0405 |

Detection method: indirect ELISA;
Primary antibody: second subclone supernatant;
Secondary antibody: goat anti-mouse IgG 1:10000;
Detection time: 2015. 11. 15;
Coating recombinant protein: 1 μg/mL.

Many cell lines were MRJP4 positive and 52 positive cell lines were selected after the fusion detection. 20 of the 52 positive cell lines were selected for the first subcloning and 14 cell lines were selected for the second subcloning after the first subcloning.

5. Screening of MRJP4-Specific Cell Lines

After detecting a cross reaction with the recombinant proteins and natural proteins, the cell lines where the cross reaction occurred were removed and finally 9 MRJP4 fusion cell lines were obtained. Parts of the results in Table 5 showed that ten of the MRJP4 cell lines had a cross reaction with the remaining four recombinant proteins.

TABLE 5

Screening results of MRJP4-specific cell lines

| Clone No. | coated with of E-MRJP4 | coated with of E-MRJP1 | coated with of E-MRJP2 | coated with of E-MRJP3 | coated with of E-MRJP5 |
|---|---|---|---|---|---|
| 6B9 | 2.3145 | 0.2142 | 0.1023 | 0.0254 | 0.0364 |
| 3B6 | 2.2035 | 0.5142 | 0.6428 | 0.1528 | 0.2415 |
| 6H9 | 2.541 | 0.1542 | 0.0142 | 0.0256 | 0.1301 |
| 6D2 | 2.3148 | 0.2031 | 0.0231 | 0.0247 | 0.0167 |
| 6F4 | 2.3694 | 0.1698 | 0.1214 | 0.1105 | 0.1324 |
| 7H8 | 2.0254 | 0.6897 | 1.3015 | 0.3183 | 0.2143 |
| 6E2 | 2.2156 | 0.2163 | 0.1324 | 0.0251 | 0.0397 |
| 4H5 | 2.2369 | 0.1974 | 0.2316 | 0.1364 | 0.0247 |
| 8C9 | 2.6987 | 0.1572 | 0.1987 | 0.1021 | 0.0471 |
| 7G8 | 2.7102 | 0.1694 | 0.201 | 0.0473 | 0.0632 |
| 6C12 | 2.3016 | 0.2015 | 0.1324 | 0.0112 | 0.103 |
| 5A2 | 2.0236 | 0.6287 | 0.9334 | 0.3142 | 0.2589 |
| 5D12 | 2.3654 | 1.0236 | 0.9123 | 0.5123 | 0.3169 |
| 5D8 | 2.1326 | 0.4163 | 0.2563 | 0.3425 | 0.2269 |
| 5D10 | 1.3692 | 1.023 | 0.8142 | 0.4598 | 0.3148 |
| 5E9 | 2.3694 | 0.4812 | 0.7105 | 0.3126 | 0.2941 |
| 6B10 | 1.0258 | 0.6125 | 0.2163 | 0.112 | 0.1987 |
| 6D10 | 1.9643 | 0.0125 | 0.3615 | 0.241 | 0.2643 |
| 2D2 | 2.3649 | 0.633 | 0.4206 | 0.3154 | 0.2215 |
| 7D11 | 2.2015 | 0.915 | 0.5231 | 0.4215 | 0.236 |

After the screening of the MRJP4 having a cross reaction with the recombinant proteins, 20 cell lines with better test results were selected for detecting cross reaction with the natural proteins of MRJP1 and MRJP2. The test results of cross reaction are shown in Table 6.

TABLE 6

Test results of cross reaction

| Coated with 1 µg/mL of natural E-MRJP1 | | | Coated with 1 µg/mL of natural E-MRJP2 | | |
|---|---|---|---|---|---|
| 0.0174 | 1.2561 | 0.8412 | 0.0154 | 1.0984 | 1.0362 |
| 0.0215 | 0.6415 | 0.6354 | 0.0147 | 0.7412 | 0.9412 |
| 0.0165 | 0.4289 | 0.0152 | 0.0326 | 0.6315 | 0.0327 |
| 0.0412 | 0.9871 | 0.0125 | 0.0258 | 1.0445 | 0.5305 |
| 0.0326 | 0.8125 | | 0.0251 | 0.5873 | |
| 0.0512 | 0.3615 | | 0.0216 | 0.6125 | |
| 0.6489 | 0.0152 | | 1.7423 | 0.0132 | |
| 1.2364 | 0.0014 | | 0.9458 | 0.0236 | |

As shown in Table 6, eleven of the MRJP4 cell lines had a cross reaction with the natural proteins of MRJP1 and MRJP2. So nine of the MRJP4-specific fusion cell lines were remained.

6. Identification of Nine Determined Cell Lines and Subtypes Thereof

Nine cell lines, which stably secrete positive antibodies and do not have a cross reaction with MRJP1 and MRJP2, selected from the subcloning stage were inoculated in 24-well plates for expanded culturing. After the expanding culturing, each supernatant was collected for antigen detection and the stability was verified by ELISA gradient dilution and western blotting. The cells were collected for expanded culturing in a 10 cm culture dish. Then, the supernatant was collected and the titer of the antibody was detected. One to three cell lines with higher titer were selected and cultured in cell culture bottles for cryopreservation. The identification results of 9 determined cell lines and subtypes thereof are shown in Table 7.

TABLE 7

Identification results of 9 determined cell lines and subtypes thereof

| Cell Line No. | Subtype |
|---|---|
| 6B9 2D11 | IgG2a |
| 6H9 2B8 | IgG2a |
| 6D2 1D11 | IgG2a |
| 6F4 2C6 | IgG2a |
| 6E2 2C2 | IgG2a |
| 4H5 1D5 | IgG2b |
| 8C9 3B10 | IgG2b |
| 7G8 3D8 | IgG2b |
| 6C12 3C3 | IgG2b |

7. Identification of Cryopreserved Cell Lines

After the cell lines were cryopreserved, one tube of the cryopreserved cell lines in the same batch should be recovered for identification. The identification criteria were as follows: 1. The number of living cells recovered was equal to or more than 1 million cells/tube. 2. Viable cells in the living cells were equal to or more than 500,000 cells/line. 3. In the recovered cells, there should be no microorganisms (such as bacteria, fungi, mycoplasma, etc.) other than cells of the cell line. 4. After growing to a certain number, the well-grown recovered cells were selected to be cultured in plates for monoclone counting and the antibody-secreting ability of the monoclone was detected whether all the antibodies were positive or the antibody was secreted. 5. The cell culture supernatant also needs to be subjected to ELISA to determine whether positive antibodies were secreted and to be subjected to identification through western blotting. The identification results are shown in FIG. 1.

8. Ascites Preparation

Ascites preparation: a mouse was injected intraperitoneally with pristane or liquid paraffin and hybridoma cells were inoculated into the peritoneal cavity of the mouse one week later. After the cells were determined, the determined cells were subjected to an expansion culture in a medium containing 10% fetal bovine serum. When the cell density reached $1\times10^6$-$2\times10^6$/mL, the cells were centrifuged at 800 rpm and the precipitate was collected, resuspended in PBS, and intraperitoneally injected into the mouse (injected with liquid paraffin). After 7-10 days, the ascites was collected for purification.

9. Ascites Purification

The procedure of the ascites purification is shown in Table 8.

TABLE 8

Antibody purification steps
Antibody purification procedure

| Process | Reagents and operations (brief) | Reaction time |
|---|---|---|
| 1. Project name | | / |
| 2. Affinity chromatography column | Protein A | / |
| 3. Chromatographic column pretreatment | Washing with 10 column bed volumes of deionized water at 1 mL/min; and washing with 10 column volumes of 1% sodium acetate (NaAc) at 1 mL/min. | 1.5 hours |

TABLE 8-continued

Antibody purification steps
Antibody purification procedure

| Process | Reagents and operations (brief) | Reaction time |
|---|---|---|
| 4. Sample loading | Filtering 10 mL of the ascites through 0.22 μm filter membrane and adding 40 mL of 1% NaAc to obtain a sample; and loading the sample at 0.5 mL/min. | 3.5 hours |
| 5. Washing | Rinsing with 1% NaAc at 4 mL/min until no protein flows out. | 0.5 hours |
| 6. Antibody elution | Rinsing with 3.5% glacial acetic acid and collecting the eluted product until no protein flows out. | / |
| 7. pH adjustment | Adjusting the pH of the eluted product to neutral with saturated solution of sodium carbonate. | / |
| 8. Sample concentration | Concentrating by ultrafiltration to about 10 mL with a 10 kDa ultrafiltration tube. | / |
| 9. Dialysis | Dialysing with 5 L of 1 × PBS overnight and changing the solution one time next day. | / |
| 10. Chromatography column washing | Rinsing the chromatography column with deionized water to neutral. | / |
| 11. Chromatography column storage | Rinsing the chromatography column with 5 times column bed volumes of 20% ethanol and then sealing at 4° C. | / |
| 12. Addition of preservative/glycerin/BSA | / | / |

Figure 2:
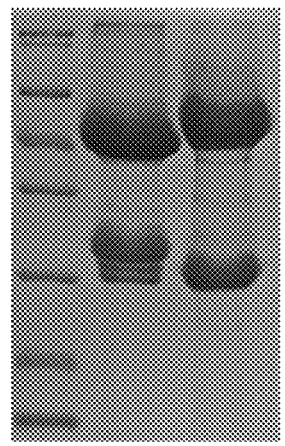
FIG. 2 shows detection results of sodium dodecyl sulfate-polyacrylamide gel electrophoresis (SDS-PAGE) of antibody 6H9 and antibody 8C9 ascites after purification, wherein, a concentration of the Marker is 0.1 mg/mL, and a loading quantity of the Marker is 5 μL; M: Marker with a molecular weight of 116 kDa, 66.2 kDa, 45 kDa, 35 kDa, 25 kDa, 18.5 kDa, and 14.5 kDa, from top to bottom; lane 1: the antibody 6H9 with a loading quantity of 5 μL; and lane 2: the antibody 8C9 with a loading quantity of 5 μL.

The data of the antibody yield after the ascites purification are shown in Table 9 and the detection results of SDS-PAGE are shown in FIG. 2.

TABLE 9

Antibody yield after ascites purification

| Clone number of cell line | Ascites volume | Antibody yield |
|---|---|---|
| 6H9 | 3 mL | 2.5 mg |
| 8C9 | 2 mL | 6 mg |

Detection results of SDS-PAGE: the antibody 6H9 had a concentration of about 2.5 mg/mL and a purity of 90%. The antibody 8C9 had a concentration of about 4 mg/mL and a purity of 90%.

10. Detection of Antibody Titer

Detection method: basic titer was detected by indirect ELISA.

Antigen coating: the antigen diluted to 2 μg/mL with a coating solution was added into a 96-well polystyrene reaction plate at 100 μL/well and placed at 4° C. overnight.

Washing: the solution in the wells was discarded on the next day and the wells was washed with a washing solution three times.

Blocking: the wells were added with a blocking solution at 150 μL/well and placed at room temperature for 0.5 hours.

Washing: the wells were washed with the washing solution three times.

Addition of the sample to be tested (primary antibody): antiserum (the blood was taken and placed at 4° C. overnight and then centrifuged at 4000 r/min for 10 min to obtain the supernatant) was added. The antiserum was doubling diluted at 1:200, 1:400, 1:800, 1:1600, 1:3200, 1:6400, 1:12800, and so on, using a sample diluent (serum blank was used as a negative control) and the diluted antiserum was added at 100 μL/well and incubated for 1 hour.

Washing: the wells were washed with the washing solution three times.

Addition of enzyme-labeled anti-antibody: the wells were added with HRP-labeled goat anti-mouse IgG (1:5000, diluted with an enzyme diluent) at 100 μL/well and incubated for 40 min at 37° C.

Washing: the wells were washed five times with the washing solution and two times with distilled water.

Color development: the wells were added with freshly prepared substrate solution at 100 μL/well and placed in dark at room temperature for 5-30 min.

Stop reaction and colorimetric assay: the wells were added with the stop solution at 50 μL/well. The solution turned yellow and the absorbance of each well was measured with a micro-plate reader at 450 nm.

Figure 3:
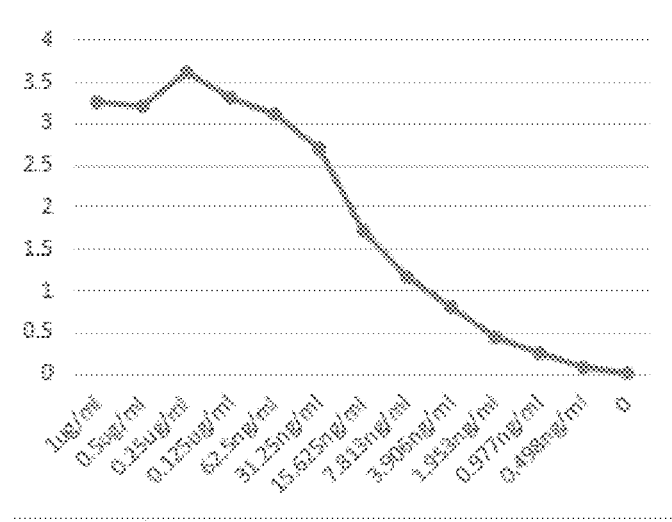
FIG. 3 shows a result of a titer detection of antibody 6H9.

The results of the titer detection of the antibody 6H9 are shown in Table 10 and FIG. 3.

Figure 4:
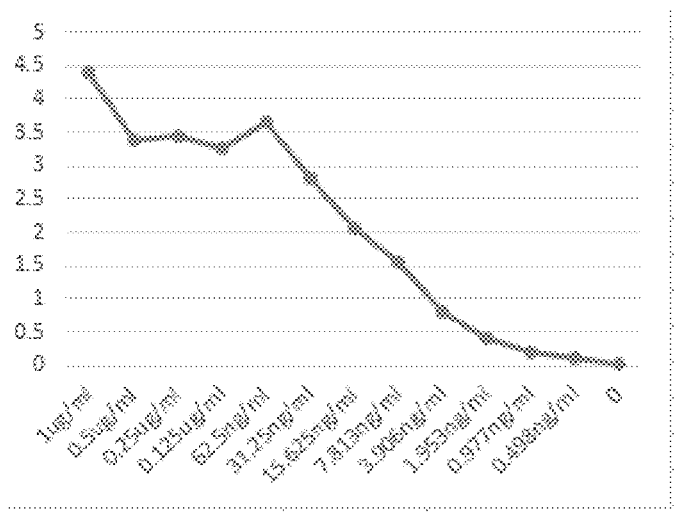
FIG. 4 shows a result of a titer detection of antibody 8C9.

The results of the titer detection of the antibody 8C9 are shown in Table 11 and FIG. 4.

TABLE 10

The results of the titer detection of antibody 6H9

| Cell line number | Primary antibody concentration | OD Value |
|---|---|---|
| 6H9 2B8 | 1 μg/mL | 3.2636 |
| | 0.5 μg/mL | 3.2206 |
| | 0.25 μg/mL | 3.6263 |
| | 0.125 μg/mL | 3.3053 |
| | 62.5 ng/mL | 3.1116 |
| | 31.25 ng/mL | 2.6988 |
| | 15.625 ng/mL | 1.7319 |
| | 7.813 ng/mL | 1.1693 |
| | 3.906 ng/mL | 0.8084 |
| | 1.953 ng/mL | 0.461 |
| | 0.977 ng/mL | 0.2496 |
| | 0.498 ng/mL | 0.0912 |
| | 0 | 0.0199 |

TABLE 11

The results of the titer detection of antibody 8C9

| Cell line number | Primary antibody concentration | OD Value |
|---|---|---|
| 8C9 3B10 | 1 μg/mL | 4.394 |
| | 0.5 μg/mL | 3.3808 |
| | 0.25 μg/mL | 3.4493 |
| | 0.125 μg/mL | 3.2723 |
| | 62.5 ng/mL | 3.6673 |
| | 31.25 ng/mL | 2.8093 |
| | 15.625 ng/mL | 2.0596 |
| | 7.813 ng/mL | 1.5505 |
| | 3.906 ng/mL | 0.8127 |
| | 1.953 ng/mL | 0.4073 |
| | 0.977 ng/mL | 0.2035 |
| | 0.498 ng/mL | 0.1165 |
| | 0 | 0.0275 |

Figure 5:
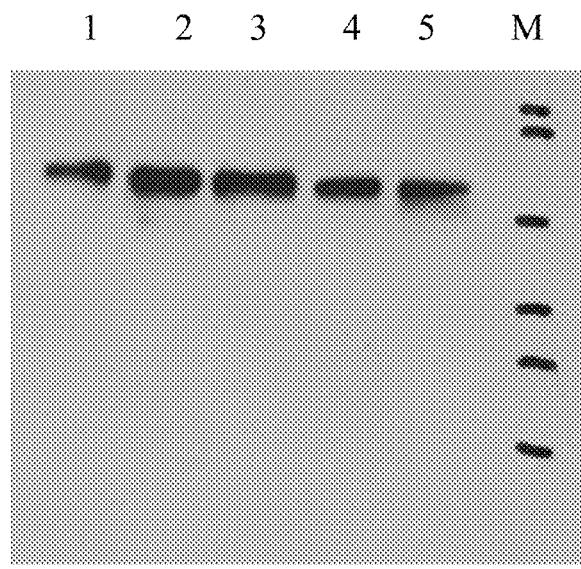
FIG. 5 shows a western blot (WB) verification of a sample of a royal jelly by using antibodies; all lanes are loaded with 15 μl of the sample of the royal jelly and 6×loading buffer; lane 1: 6E2 2C2 antibody at a 1/1000 dilution; lane 2: 7G8 3B8 antibody at a 1/1000 dilution; lane 3: 6H9 2B8 antibody at a 1/1000 dilution; lane 4: 4H5 1D5 antibody at a 1/1000 dilution; lane 5: 8C9 3B10 antibody at a 1/1000 dilution; secondary antibody: IgG (H+L)-HRP conjugate (at a 1:5000 dilution); M: Marker with a molecular weight of 120 kDa, 85 kDa, 50 kDa, 35 kDa, 25 kDa, and 20 kDa, from top to bottom.

The royal jelly sample was verified with the antibody by the western blotting and the results are shown in FIG. 5.

11. Specific Detection of Antibody

Figure 6:
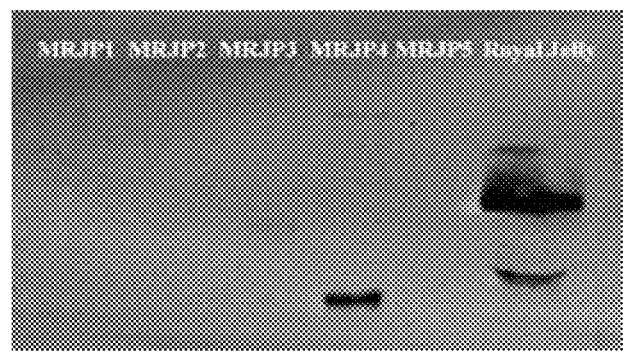
FIG. 6 shows a detection result of an antibody specificity of 8C9 cell line.
Figure 7:
FIG. 7 shows a detection result of an antibody specificity of 6H9 cell line.

The results of the specific detection of the antibody 8C9 are shown in FIG. 6. The results of the specific detection of the antibody 6H9 are shown in FIG. 7. The results of the specific detections showed that the antibody 6H9 and the antibody 8C9 were only reacted with the MRJP4, respectively, and did not have a cross reaction with the MRJP1, MRJP2, MRJP3, and MRJP5 proteins.

IV. Antibody Epitope Detection and Antibody Pairing and Screening

1. Antibody Pairing for Recognizing Different Epitopes by Blocking Experiment

Specific steps were as follows:

1.1 After the detection of the affinity and the sample, the antibody secreted by 8C9 cell line was selected and labeled with a biotin. And the optimal dilution ratio was determined.

1.2 Coating: the corresponding antigen was diluted to a concentration of 1 μg/mL with a carbonate buffer solution (CBS) for coating at 100 μL/well and 37° C. for 2 hours or 4° C. overnight.

1.3 Blocking: PBS containing 5% skimmed milk powder or PBS containing 2% BSA was used for blocking at 37° C. for 1 hour or 4° C. overnight.

1.4 Primary antibody: the labeled antibody and the detection antibody were diluted according to the dilutions (1:1000 and 1:2000) obtain by a checkerboard method. Negative control: 50 μL labeled antibody+50 μL autoantibody. Positive control: 50 μL labeled antibody+50 μL irrelevant antibody. 1.5 Secondary antibody: goat anti-mouse IgG or rabbit anti-mouse IgG was added at 100 μL/well and 37° C. for 1 hour.

1.6 Substrate: an appropriate substrate selected according to the labeled enzyme was added at 100 μL/well and reacted for 10 min.

1.7 Color development, termination, and reading were performed.

The dilution ratio of the 8C9 biotin-labeled antibody was first determined by a dilution gradient test. The results of the dilution gradient test are shown in Table 12.

TABLE 12

Results of dilution gradient test on 8C9 biotin-labeled antibody

| Antibody NO. | Dilution ratio of primary antibody | OD value |
|---|---|---|
| 8C93B10 biotin-labeled antibody | 1/1000 | 4.4.82 |
| | 1/2000 | 3.1092 |
| | 1/4000 | 4.4222 |
| | 1/8000 | 4.373 |
| | 1/16000 | 3.5095 |
| | 1/32000 | 3.0833 |
| | 1/64000 | 2.2718 |
| | 0 | 0.0057 |

According to the above results, 1/50,000 was selected as the dilution ratio of the labeled antibody and the blocking experiment was performed next.

The detection method for the blocking experiment was an indirect competitive ELISA as follows.

The antibody diluted to a concentration of 1 μg/mL with a coating buffer (CB) was used for direct coating. The primary antibody detection is performed with 50 μL labeled antibody+50 μL detection antibody. The negative control is 50 μL labeled antibody+50 μL autoantibody. The positive control is 50 μL labeled antibody+50 μL SP2/0 culture supernatant.

The method of the blocking experiment is shown in Table 13 and the screening results are shown in Table 14.

TABLE 13

Results of antibody pairing for recognizing different epitopes

Detection method: indirect competition ELISA
Coating concentration: 1 μg/mL, direct coating using CB;
Primary antibody detection is performed with
50 μL labeled antibody + 50 μL detection
antibody; the negative control is 50 μL labeled
antibody + 50 μL autoantibody; and the
positive control is 50 μL labeled antibody + 50 μL
SP2/0 culture supernatant;
Enzyme-labeled secondary antibody goat anti-mouse IgG: 1/10000.

TABLE 14

Screening results of blocking experiment

| Number of detection antibody | 8C93B10 biotin-labeled antibody with a dilution ratio of 1/50000 |
|---|---|
| 4H5 1D5 | 0.101 |
| 6E2 2C2 | 0.1154 |
| 6H9 2B8 | 1.5701 |
| 7C8 3B8 | 0.2218 |
| Negative control | 0.1047 |
| Positive control | 1.8032 |

The results of the blocking experiment in Table 14 showed that 6H9 and the labeled antibody had different epitopes. Ascites preparation, antibody purification and labeling experiments were performed on 6H9 having different epitopes with the 8C9 labeled antibody. The titer detection showed that the two antibodies both had high affinity and were used for R&D experiments at the next stage.

2. Determination of pairing standard curve and sample detection of antibody pairing Preliminary titration: a match-paired antibodies 8C9 and 6H9 were selected for a test of the preliminary titration.

Test method: a double-anti-sandwich method was used. The 6H9 was diluted to a concentration of 2 μg/mL with CB and was used for direct coating. The 8C9 was used as a detection antibody and was labeled with biotin and used at a 1:2000 dilution. HRP was used at a 1:4000 dilution. The reaction time of the test was 2 hours+1 hour+1 hour+20 min. The results in the test of the preliminary titration on the match-paired antibodies are shown in Table 15.

TABLE 15

Results of the test of the preliminary titration on the match-paired antibodies by the double-anti-sandwich method

| Standard curve | OD1 | OD2 | Mean OD |
|---|---|---|---|
| 1 μg/mL | 3.1633 | 3.2145 | 3.1889 |
| 500 ng/mL | 3.1483 | 3.1579 | 3.1531 |
| 100 ng/mL | 1.6819 | 1.6247 | 1.6533 |
| 50 ng/mL | 1.0125 | 0.9875 | 1.0000 |
| 10 ng/mL | 0.4532 | 0.4614 | 0.4573 |
| 5 ng/mL | 0.1798 | 0.1249 | 0.1524 |
| 2.5 ng/mL | 0.0357 | 0.0426 | 0.0392 |
| 0 | 0.1001 | 0.1053 | 0.1027 |

Checkerboard titration: a dilution ratio of the captured antibody, labeled antibody and sample was determined.

Test method: the double-anti-sandwich method was used. The 6H9 was diluted with the CB and was used for direct coating. The 8C9 was used as a detection antibody and was labeled with biotin. HRP was used at a 1:4000 dilution. The reaction time of the test was 2 hours+1 hour+1 hour+20 min.

The results of the dilution ratio of the captured antibody, labeled antibody and sample are shown in Table 16.

TABLE 16

Results of the dilution ratio of the captured antibody, labeled antibody and sample by the checkerboard titration

| Standard curve (ng) | Coating with 1 µg/mL of 6H9, and detecting with 8C9-Bio diluted at 1:4000 | | | Coating with 2 µg/mL of 6H9, and detecting with 8C9-Bio diluted at 1:8000 | | | Coating with 4 µg/mL of 6H9, and detecting with 8C9-Bio diluted at 1:8000 | | |
|---|---|---|---|---|---|---|---|---|---|
| | OD1 value | OD2 value | Mean OD value | OD1 value | OD2 value | Mean OD value | OD1 value | OD2 value | Mean OD value |
| 200 | 2.7346 | 2.8105 | 2.7726 | 2.2139 | 2.2729 | 2.2434 | 2.2574 | 2.3105 | 2.2840 |
| 100 | 1.5788 | 1.5934 | 1.5861 | 1.2273 | 1.2918 | 1.2595 | 1.3571 | 1.3057 | 1.3314 |
| 50 | 0.9004 | 1.0231 | 0.9618 | 0.7422 | 0.7678 | 0.7550 | 0.7523 | 0.7712 | 0.7618 |
| 25 | 0.4642 | 0.5102 | 0.4872 | 0.4361 | 0.4536 | 0.4449 | 0.4033 | 0.4468 | 0.4251 |
| 12.5 | 0.2524 | 0.2631 | 0.2578 | 0.2453 | 0.2665 | 0.2559 | 0.2566 | 0.2615 | 0.2591 |
| 6.25 | 0.1904 | 0.1849 | 0.1877 | 0.1574 | 0.1425 | 0.1500 | 0.1818 | 0.1634 | 0.1726 |
| 3.125 | 0.1577 | 0.1624 | 0.1601 | 0.1143 | 0.1103 | 0.1123 | 0.1228 | 0.1143 | 0.1186 |
| 0 | 0.0821 | 0.0156 | 0.0489 | 0.0656 | 0.0185 | 0.0421 | 0.0985 | 0.0178 | 0.0582 |

Figure 8:
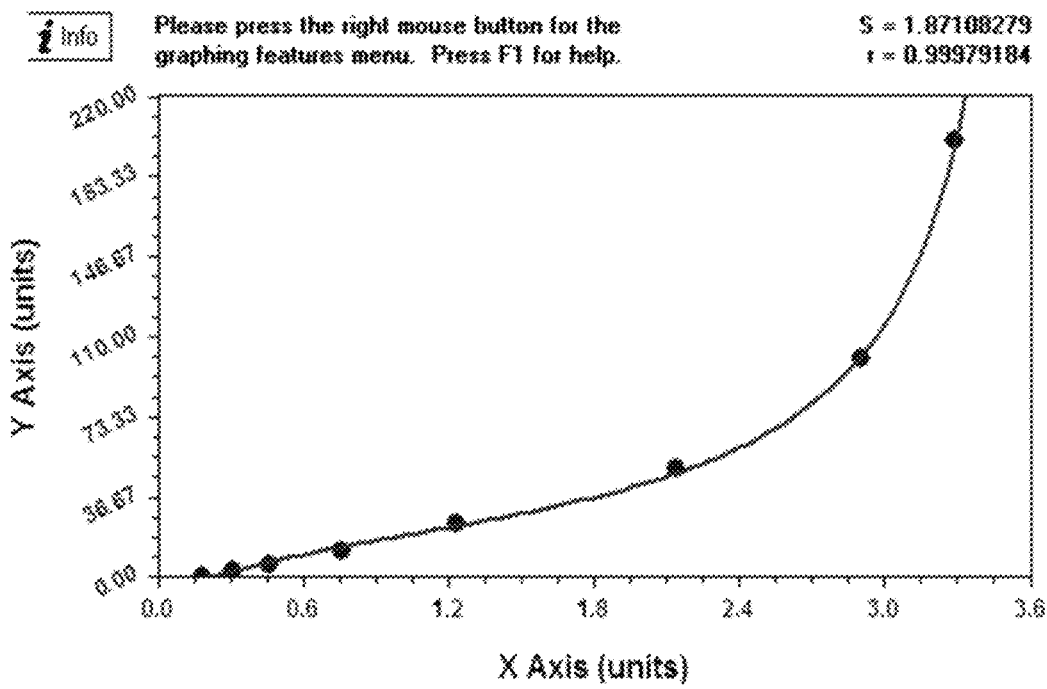
FIG. 8 shows a standard curve of a preliminary sample detected at different detecting conditions.

According to the above determined dilution conditions for the coating antibody and the detection antibody, the preliminary sample detection was performed as follows:

Test method 1: the double-anti-sandwich method was used. The 6H9 diluted to a concentration of 1 µg/mL with CB and was used for direct coating. The 8C9 was used as a detection antibody and was labeled with biotin, at a 1:2000 dilution. HRP was used at a 1:4000 dilution. The reaction time of the test was 2 hours+1 hour+1 hour+20 min. The results of the preliminary sample detection are shown in Table 17. The standard curve of the preliminary sample detection in different test conditions is shown in FIG. 8.

TABLE 17

Results of preliminary sample detection

| Standard curve (ng/mL) | OD1 value | OD2 value | Mean OD | Sample | OD value |
|---|---|---|---|---|---|
| 200 | 3.1848 | 3.0542 | 3.1195 | Royal jelly 1:300 | 3.095 |
| 100 | 2.9796 | 2.8795 | 2.9296 | Royal jelly 1:300 | 3.177 |
| 50 | 2.1159 | 2.2105 | 2.1632 | Royal jelly 1:300 | 3.4243 |
| 25 | 1.2531 | 1.2634 | 1.2583 | Royal jelly 1:300 | 2.8752 |
| 12.5 | 0.7618 | 0.8123 | 0.7871 | Royal jelly 1:300 | 3.7793 |
| 6.25 | 0.47 | 0.4916 | 0.4808 | | |
| 3.125 | 0.3462 | 0.3215 | 0.3339 | | |
| 0 | 0.2185 | 0.2018 | 0.2102 | | |

Figure 9:
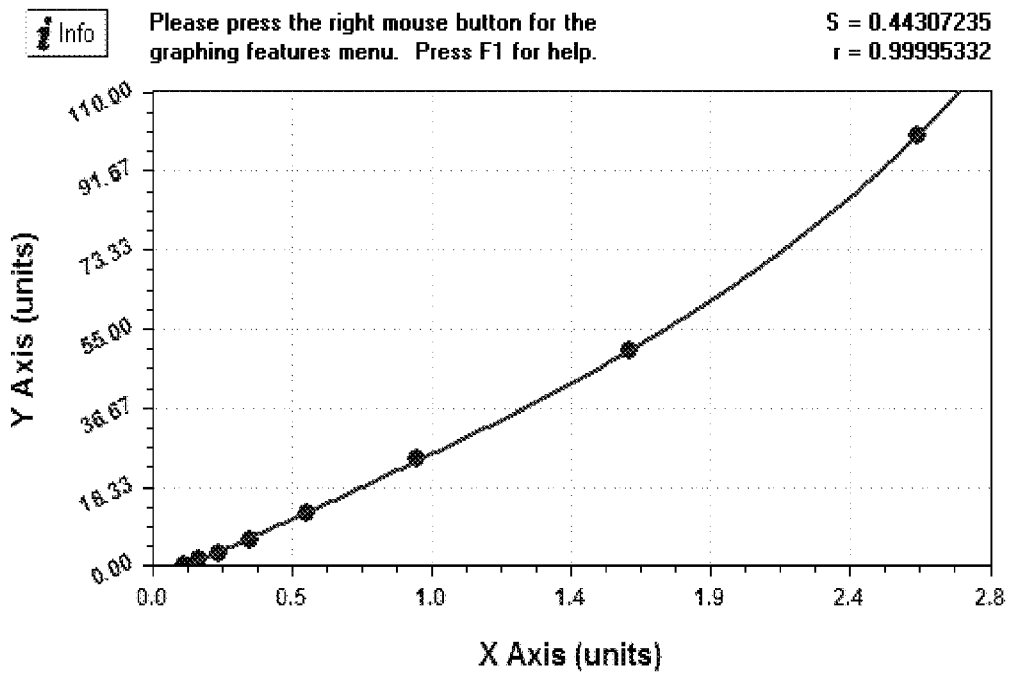
FIG. 9 shows another standard curve of preliminary sample detected at different detecting conditions.

Test method 2: the double-anti-sandwich method was used. The 6H9 diluted to a concentration of 1 µg/mL with CB and was used for direct coating. The 8C9 was used as a detection antibody and was labeled with biotin, at a 1:3000 dilution. HRP was used at a 1:4000 dilution. The reaction time of the test was 2 hours+1 hour+1 hour+20 min. The results of the preliminary sample detection are shown in Table 18. The standard curve of the preliminary sample detection in different test conditions is shown in FIG. 9.

TABLE 18

Results of preliminary sample detection

| Standard curve (ng/mL) | OD1 value | OD2 value | Mean OD | Sample | OD value |
|---|---|---|---|---|---|
| 100 | 2.5877 | 2.6043 | 2.5960 | Royal jelly 1:1500 | 1.8496 |
| 50 | 1.6016 | 1.6473 | 1.6245 | Royal jelly 1:3000 | 1.4151 |
| 25 | 0.8974 | 0.9123 | 0.9049 | Royal jelly 1:6000 | 1.1269 |

TABLE 18-continued

Results of preliminary sample detection

| Standard curve (ng/mL) | OD1 value | OD2 value | Mean OD | Sample | OD value |
|---|---|---|---|---|---|
| 12.5 | 0.5165 | 0.5548 | 0.5357 | Royal jelly 1:12000 | 0.8302 |
| 6.25 | 0.3251 | 0.3625 | 0.3438 | Royal jelly lyophilized powder 1:1500 | 1.3173 |
| 3.125 | 0.2283 | 0.2432 | 0.2358 | Royal jelly lyophilized powder 1:3000 | 0.9016 |
| 1.563 | 0.2008 | 0.1352 | 0.1680 | Royal jelly lyophilized powder 1:6000 | 0.6244 |
| 0 | 0.1269 | 0.1126 | 0.1198 | Royal jelly lyophilized powder 1:12000 | 0.3529 |

Figure 10:
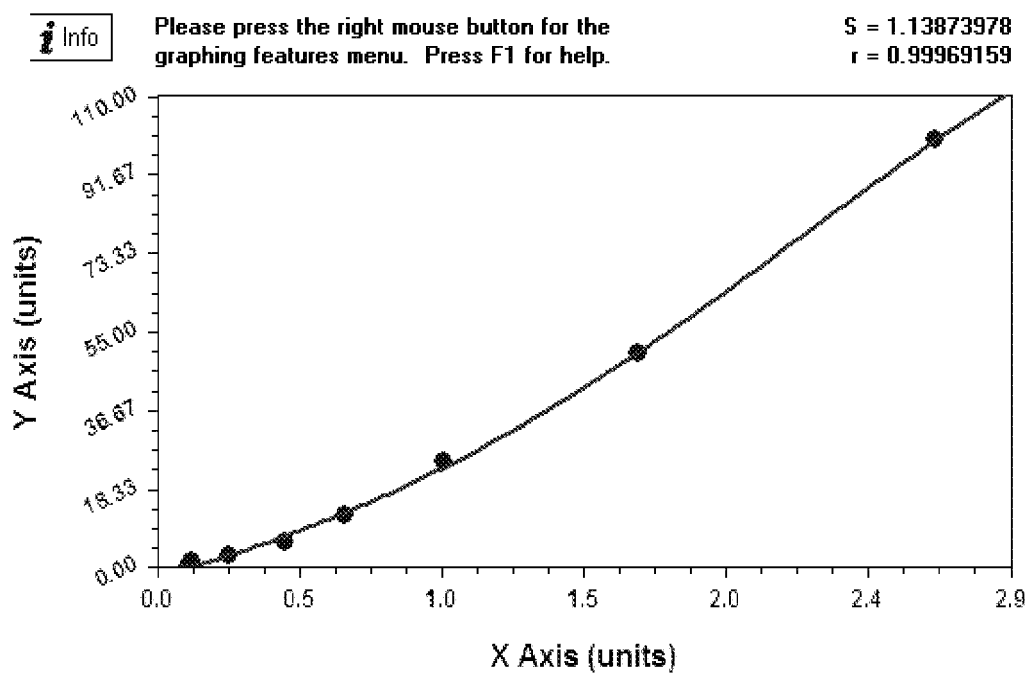
FIG. 10 shows a standard curve of re-measurement of a lyophilized standard.

Retest of the lyophilized standard: the double-anti-sandwich method was used. The 6H9 was diluted to a concentration of 1 µg/mL with CB and was used for direct coating. The 8C9 was used as a detection antibody and was labeled with biotin, at a 1:3000 dilution. HRP was used at a 1:4000 dilution. The reaction time of the test was 2 hours+1 hour+1 hour+20 min. The results of the retest of the lyophilized standard are shown in Table 19 and Table 20. The standard curve in the retest of the lyophilized standard is shown in FIG. 10.

TABLE 19

Results of lyophilized standards

| Standard curve (ng/mL) | OD1 value | OD2 value | Mean OD | Sample | OD value |
|---|---|---|---|---|---|
| 100 | 2.6571 | 2.6952 | 2.6762 | Royal jelly 1:1600 | 1.6968 |
| 50 | 1.6878 | 1.6248 | 1.6563 | Royal jelly 1:3200 | 0.9778 |
| 25 | 0.985 | 1.0025 | 0.9938 | Royal jelly 1:6400 | 0.6108 |
| 12.5 | 0.614 | 0.6935 | 0.6538 | Royal jelly 1:12800 | 0.4542 |
| 6.25 | 0.4356 | 0.4636 | 0.4496 | Royal jelly 1:25600 | 0.3245 |
| 3.125 | 0.2819 | 0.2359 | 0.2589 | Royal jelly 1:51200 | 0.2542 |
| 1.563 | 0.1404 | 0.1259 | 0.1332 | Royal jelly 1:102400 | 0.2344 |
| 0 | 0.1293 | 0.1068 | 0.1181 | | 0.1801 |

TABLE 20

Quantitative Results of Samples

| Sample | OD value | Concentration calculated by substituting into a formula (ng/mL) | Actual concentration (ng/mL) |
|---|---|---|---|
| Royal jelly 1:1600 | 1.6968 | 52.20017203 | 83520.27525 |
| Royal jelly 1:3200 | 0.9778 | 23.14169658 | 74053.42907 |
| Royal jelly 1:6400 | 0.6108 | 11.84138043 | 75784.83478 |
| Royal jelly 1:12800 | 0.4542 | 7.723859319 | 98865.39928 |
| Royal jelly 1:25600 | 0.3245 | 4.610880958 | 118038.5525 |
| Royal jelly 1:51200 | 0.2542 | 3.030799997 | 155176.9598 |
| Royal jelly 1:102400 | 0.2344 | 2.598937038 | 266131.1527 |

V. Antibody Purification

1. A chromatographic column was washed and equilibrated with 10 column volumes of PBS (or Tris-buffered saline (TBS), similarly hereinafter).

2. After the antibody-containing serum or other body fluids were centrifuged at a high speed, the supernatant was mixed with an equal volume of 2×PBS buffer and slowly added to the chromatographic column after the pH and ion concentration were adjusted.

3. 10 column volumes of PBS were used to wash until no protein was detected in the effluent.

4. 2 column volumes of 0.1 M citric acid (Citrate Acid, pH 2.7) were added for elution, the outflow tube was clamped, the permeate solution was collected after standing for 5 minutes and this was repeated three times. The concentration of the antibody was estimated by measuring OD280. When the amount of the obtained antibodies was large, the purity was determined by SDS-PAGE. 0.1 M glycine (Glycine, pH 3.0) could be used for elution as well.

5. The eluted antibody was neutralized by adding 2/5 volume of 1 M Tris with a pH of 8.0. A Millipore protein concentration tube was used to switch to a required buffer, wherein the required buffer was generally 2×PBS containing 0.02% $NaN_3$ and 1 mM ethylenediaminetetraacetic acid (EDTA).

6. The antibody solution was concentrated to a required volume and the purity was detected by SDS-PAGE, and then stored at −20° C. and avoided from freezing.

Embodiment 2 Establishment of Royal Jelly MRJP4 Double Sandwich Enzyme-Linked Immunosorbent Assay and Preparation of Royal Jelly MRJP4 ELISA Kit The detection principle of royal jelly MRJP4 double sandwich enzyme-linked immunosorbent assay was as follows: a purified antibody was used to coat a microplate to make a solid phase carrier, a sample or a standard, a biotin-labeled antibody against MRJP4. A HRP-labeled avidin were sequentially added to the microwells of the microplate coated with the antibody against the MRJP4. After the microwells were thoroughly washed, the substrate TMB was used for a color development. TMB turns blue under a catalysis of a peroxidase and finally turns yellow under an action of an acid. A color depth is positively correlated with the MRJP4 in the sample. An absorbance (optical density (OD) value) is measured at a wavelength of 450 nm using a microplate reader to calculate a concentration of the sample.

1. Diagram of Standard Curve and Linear Range of the Standard Curve 1.1 Primary Screening of a Matched Antibody Pair The specific steps were as follows:

1.1.1 Coating: the 96-well plate was coated with 2 µg/mL of the antibody and placed at 37° C. for 2 hours or 4° C. overnight.

1.1.2 Blocking: the 96-well plate was added with a blocking solution containing 2% BSA or 5% skimmed milk at 200 µL/well, placed at 37° C. for 1 hour or 4° C. overnight and then washed with TBST 4 times.

1.1.3 Standard and sample: the 96-well plate was added with the standard and the sample, as indicated in the figure at 50 µL/well, and placed at 37° C. for 2 hours.

1.1.4 Antibody binding: the 96-well plate was added with a biotin-labeled antibody at a recommended dilution ratio and 90 µL/well and placed at 37° C. for 1 hour.

1.1.5 Second antibody: the 96-well plate was currently added with the HRP-avidin with a 1:4000 dilution in a concentration at 90 µL/well and placed at 37° C. for 1 hour.

1.1.6 Substrate: the 96-well plate was added with the substrate at 90 µL/well and placed at 37° C. for 5-15 min.

1.1.7 Stop reaction and colorimetric assay: the 96-well plate was added with a stop solution at 30 µL/well. The solution turned yellow and the absorbance at 450 nm was measured with a microplate reader.

TABLE 21

Results of pairing screening

| standard curve | OD1 | OD2 | mean OD |
|---|---|---|---|
| 1 ug/ml | 3.1633 | 3.2145 | 3.1889 |
| 500 ng/ml | 3.1483 | 3.1579 | 3.1531 |
| 100 ng/ml | 1.6819 | 1.6247 | 1.6533 |
| 50 ng/ml | 1.0125 | 0.9875 | 1.0000 |
| 10 ng/ml | 0.4532 | 0.4614 | 0.4573 |
| 5 ng/ml | 0.1798 | 0.1249 | 0.1524 |
| 2.5 ng/ml | 0.0357 | 0.0426 | 0.0392 |
| 0 | 0.1001 | 0.1053 | 0.1027 |

Item NO. PA1-18100037-MRJP4
Experimental Method Double-anti-sandwich method
Coating antibody 6H9, 2 µg/mL, CB, direct coating
Detection antibody 8C9-Bio 1:2000
HRP 1:4000
Experiment reaction time 2 hours+1 hour+1 hour+20 min
Experiment date 2018-10-18
Conclusion:
1. Primary paring can be achieved
2. The highest point of checkerboard titration can be tested from 500 ng/ml The above pairing screening results in Table 23 shows that the antibody 6H9 has a relatively high sensitivity with 8C9, which meets expectations. Next, samples were directly measured and a retest was performed.

1.2 Standard Curve Setting

The principle of setting the standard curve is based on the detected concentrations of the samples. That is, the curve needs to include the range of the detected concentrations of all the samples. The concentration of the standard was fixed and different concentrations of the coating antibody, detection antibody, and the secondary antibody were selected for the checkerboard titration experiment (see Table 22) to select the appropriate concentration of each parameter.

TABLE 22

Results of checkerboard titration
Item NO. PA1-18100037-MRJP4
Experimental Method Double-anti-sandwich method
Coating antibody 6H9, CB, direct coating
Detection antibody 8C9-Bio
HRP 1:4000
Experiment reaction time 2 hours + 1 hour + 1 hour + 20 min
Experiment date 2018 Oct. 19

| | | Concentration of coating antibody 6H9 (μg/mL) | | | | | |
|---|---|---|---|---|---|---|---|
| | | 4 μl/ml | | 2 μl/ml | | 1 μg/ml | |
| | | Protein (ng/ml) | OD value | Protein (ng/ml) | OD value | Protein (ng/ml) | OD value |
| 8C9-Bio detection antibody ratio | 1:500 | 500 | 3.0577 | 500 | 3.2155 | 500 | 3.1002 |
| | | 50 | 1.8576 | 50 | 1.534 | 50 | 1.023 |
| | 1:1000 | 500 | 4.4274 | 500 | 2.9942 | 500 | 3.347 |
| | | 50 | 0.9735 | 50 | 0.7482 | 50 | 0.4814 |
| | 1:2000 | 500 | 3.3853 | 500 | 3.3839 | 500 | 4.3881 |
| | | 50 | 0.5013 | 50 | 0.4062 | 50 | 0.2146 |
| | 1:4000 | 500 | 3.461 | 500 | 3.4539 | 500 | 3.0132 |
| | | 50 | 0.2094 | 50 | 0.2 | 50 | 0.1289 |

The specific steps were as follows:

1.2.1 Coating: a 96-well plate was coated with the antibody to be detected at 1 μg/mL, 2 μg/mL, and 4 μg/mL as indicated in Table 22 figure, and placed at 37° C. for 2 hours or 4° C. overnight.

1.2.2 Blocking: the 96-well plate was added with a blocking solution containing 2% BSA or 5% skimmed milk at 200 μL/well, placed at 37° C. for 1 hour or 4° C. overnight, and then washed with TBST 4 times.

1.2.3 Recombinant protein as a standard: the 96-well plate was added with the standard set S7 and S0 at 50 μL/well and placed at 37° C. for 2 hours.

1.2.4 Antibody binding: the 96-well plate was added with a biotin-labeled antibody at a recommended dilution ratio and 90 μL/well and placed at 37° C. for 1 hour.

1.2.5 Second antibody: the 96-well plate was currently added with the HRP-avidin with a 1:4000 dilution in a concentration at 90 μL/well and placed at 37° C. 1 hour.

1.2.6 Substrate: the 96-well plate was added with the substrate at 90 μL/well and placed at 37° C. for 5-15 min.

1.2.7 Stop reaction and colorimetric assay: the 96-well plate was added with a stop solution at 30 μL/well and the solution turned yellow. The absorbance at 450 nm was measured with a microplate reader.

1.3 Standard Curve Adjustment

The standard curve was optimized by appropriately adjusting of the concentrations of the coating antibody, detection antibody and HRP to ensure that R2 of the standard curve was equal to or more than 0.99, which is considered acceptable.

TABLE 23

Determination of first standard curve
Item NO. PA1-18100037-MRJP4
Experimental Method Double-anti-sandwich method
Coating antibody 6H9, CB, direct coating
Detection antibody 8C9-Bio
HRP 1:4000
Experiment reaction time 2 hours + 1 hour + 1 hour + 20 min
Experiment date 2018 Oct. 22

| | Coating with 1 μg/mL of 6H9, detecting with 8C9-Bio at 1:4000 | | | Coating with 2 μg/mL of 6H9, detecting with 8C9-Bio at 1:8000 | | | Coating with 4 μg/mL of 6H9, detecting with 8C9-Bio at 1:8000 | | |
|---|---|---|---|---|---|---|---|---|---|
| Standard curve (ng) | OD1 Value | OD2 Value | Mean OD Value | OD1 Value | OD2 Value | Mean OD Value | OD1 Value | OD2 Value | Mean OD Value |
| 200 | 2.7346 | 2.8105 | 2.7726 | 2.2139 | 2.2729 | 2.2434 | 2.2574 | 2.3105 | 2.2840 |
| 100 | 1.5788 | 1.5934 | 1.5861 | 1.2273 | 1.2918 | 1.2595 | 1.3571 | 1.3057 | 1.3314 |
| 50 | 0.9004 | 1.0231 | 0.9618 | 0.7422 | 0.7678 | 0.7550 | 0.7523 | 0.7712 | 0.7618 |
| 25 | 0.4642 | 0.5102 | 0.4872 | 0.4361 | 0.4536 | 0.4449 | 0.4033 | 0.4468 | 0.4251 |
| 12.5 | 0.2524 | 0.2631 | 0.2578 | 0.2453 | 0.2665 | 0.2559 | 0.2566 | 0.2615 | 0.2591 |
| 6.25 | 0.1904 | 0.1849 | 0.1877 | 0.1574 | 0.1425 | 0.1500 | 0.1818 | 0.1634 | 0.1726 |
| 3.125 | 0.1577 | 0.1624 | 0.1601 | 0.1143 | 0.1103 | 0.1123 | 0.1228 | 0.1143 | 0.1186 |
| 0 | 0.0821 | 0.0156 | 0.0489 | 0.0656 | 0.0185 | 0.0421 | 0.0985 | 0.0178 | 0.0582 |

The test results of the above three conditions showed that the standard curves are good, but the low value is relatively low. The standard curve was further adjusted according to the test results.

TABLE 24

Determination of second standard curve

Item NO. PA1-18100037-MRJP4
Experimental Method
Double-anti-sandwich
method Coating antibody 6H9,
1 μg/mL, CB, direct coating
Detection antibody 8C9-Bio,
detecting at 1:2000 HRP 1:4000
Experiment reaction time 2 hours +
1 hour + 1 hour + 20 min
Experiment date 2018 Oct. 25

Conclusion:
The highest value of the standard curve can continue to be reduced. The sample of the royal jelly to be detected has a value, but the detected value is relatively high, which may be caused by uneven mixing during absorbing the sample.

| Standard curve(ng/ml) | OD Value | OD2 Value | Mean OD Value | sample | OD Value |
|---|---|---|---|---|---|
| 200 | 3.1843 | 3.0542 | 3.1195 | Royal jelly 1:300 | 3.095 |
| 100 | 2.9796 | 2.8795 | 2.9296 | Royal jelly 1:300 | 3.177 |
| 50 | 2.1159 | 2.2105 | 2.1632 | Royal jelly 1:300 | 3.4243 |
| 25 | 1.2531 | 1.2634 | 1.2583 | Royal jelly 1:300 | 2.8752 |
| 12.5 | 0.7618 | 0.8123 | 0.7871 | | 3.7793 |
| 6.25 | 0.47 | 0.4916 | 0.4808 | | |
| 3.125 | 0.3462 | 0.3215 | 0.3339 | | |
| 0 | 0.2185 | 0.2018 | 0.2102 | | |

The results show that the highest value of the standard curve can continue to be reduced. The sample of the royal jelly to be detected has a value, but the detected value is relatively high, which may be caused by uneven mixing during absorbing the sample.

TABLE 25

Determination of third standard curve
Item NO. PA1-18100037-MRJP4
Experimental Method Double-anti-sandwich method
Coating antibody 6H9, 1 μg/mL, CB, direct coating
Detection antibody 8C9-Bio, detecting at 1:3000
HRP 1:4000
Experiment reaction time 2 hours + 1 hour + 1 hour + 20 min
Experiment date 2018 Oct. 29

| Standard curve(ng/ml) | OD1 Value | OD2 Value | Mean OD Value | sample | OD Value |
|---|---|---|---|---|---|
| 100 | 2.5887 | 2.6043 | 2.5690 | Royal jelly 1:1500 | 1.8496 |
| 50 | 1.6016 | 1.6473 | 1.6245 | Royal jelly 1:3000 | 1.4151 |
| 25 | 0.8974 | 0.9123 | 0.9049 | Royal jelly 1:6000 | 1.1269 |
| 12.5 | 0.5165 | 0.5548 | 0.5357 | Royal jelly 1:12000 | 0.8302 |
| 6.25 | 0.3251 | 0.3625 | 0.3438 | Lyophilized powder of Royal jelly 1:150 | 1.3173 |
| 3.125 | 0.2283 | 0.2432 | 0.2358 | Lyophilized powder of Royal jelly 1:300 | 0.9016 |
| 1.563 | 0.2008 | 0.1352 | 0.1680 | Lyophilized powder of Royal jelly 1:600 | 0.6244 |
| 0 | 0.1269 | 0.1126 | 0.1198 | Lyophilized powder of Royal jelly 1:120 | 0.3529 |

From the linearity of the standard curve, the condition of coating at 1 μg/ml and detecting at 1:3000 is more suitable. The sample was tested at different dilution ratios and the OD value decreased linearly with the decrease of the dilution ratio, meeting expectations. The form of the standard was changed and the stability was tested.

2. Establishment in Detection and Evaluation Method of Sample 2.1 Sample Pretreatment.

2.1.1 The sample was pretreated according to the type of the sample.

2.1.2 Repeated wells were set in the test.

2.1.3 For some samples with higher content, the sample should be diluted and then performed with a gradient test.

TABLE 26

Sample detection of MRJP4
Item NO. PA1-18100037-MRJP4
Experimental Method Double-anti-sandwich method
Coating antibody 6H9, 1 μg/mL, CB, directly coating
Detection antibody 8C9-Bio, detecting at 1:3000
HRP 1:4000
Experiment reaction time 2 hours + 1 hour + 1 hour + 20 min
Experiment date 2018 Nov. 9

| Standard curve(ng/mL) | OD1 Value | OD2 Value | Mean OD Value | sample | OD Value |
|---|---|---|---|---|---|
| 100 | 2.6571 | 2.6952 | 2.6762 | Royal jelly 1:6500 | 1.6968 |
| 50 | 1.6678 | 1.6248 | 1.6563 | Royal jelly 1:3200 | 0.9778 |
| 25 | 0.985 | 1.0025 | 0.9938 | Royal jelly 1:6400 | 0.6108 |
| 12.5 | 0.614 | 0.6935 | 0.6538 | Royal jelly 1:12800 | 0.4542 |
| 6.25 | 0.4536 | 0.4636 | 0.4496 | Royal jelly 1:25600 | 0.3245 |
| 3.125 | 0.2819 | 0.2359 | 0.2589 | Royal jelly 1:51200 | 0.2542 |
| 1.563 | 0.1404 | 0.1259 | 0.1332 | Royal jelly 1:102400 | 0.2344 |
| 0 | 0.1293 | 0.1068 | 0.1181 | Sample dilution | 0.1801 |

3. Assessment of ELISA 3.1 Stability 3.1.1 Stability Test

Stabilities after 4 days and 7 days were tested by the following method: two sets of a coated plate (coated with an antibody), a standard (a lyophilized powder), and a detection antibody at an intermediate concentration were placed in a 37° C. incubator, respectively. One set was taken out after 4 days and the other set was taken out after 7 days. After 7 days, standard curves of the two sets of raw materials subjected to a thermal damage test were made and compared with that of another set of the raw materials placed at 4° C. The reduction rate of OD value was calculated.

3.1.2 Evaluation Criteria

After the thermal damage test of the raw materials, at the 37° C. incubator for 7 days, the reduction rate equal to or less than 30% was considered to have a qualified stability.

TABLE 27

Results of thermal damage test at 37° C.
Item NO. PA1-18100037-MRJP4
Experimental Method Double-anti-sandwich method
Coating antibody 6H9, 1 μg/mL, CB, directly coating
Detection antibody 8C9-Bio, detecting at 1:3000
HRP 1:4000
Experiment reaction time 2 hours + 1 hour + 1 hour + 20 min
Experiment date 2018 Nov. 27

| Standard curve(ng/mL) | OD Value- 0 day | OD Value- 4th day | OD Value- 7$^{th}$ day | rate |
|---|---|---|---|---|
| 100 | 2.872 | 2.6978 | 2.1478 | 25% |
| 50 | 1.9835 | 1.745 | 1.5274 | 23% |
| 25 | 1.271 | 1.0524 | 0.9702 | 24% |
| 12.5 | 0.7655 | 0.6855 | 0.6917 | 10% |
| 6.25 | 0.4689 | 0.4125 | 0.4834 | −3% |
| 3.125 | 0.3235 | 0.2997 | 0.2635 | 19% |
| 1.563 | 0.2388 | 0.2451 | 0.2374 | 1% |
| 0 | 0.1635 | 0.1722 | 0.1814 | −11% |

The thermal stabilities all decreased by less than 30% in 7 days, which were qualified. An intra-batch and an inter-batch assay were performed next.

3.2 Differences of Intra-Batch and Inter-Batch 3.2.1 Intra-batch coefficient of variation (CV): requirement≤8%, method: the coefficient of variation was obtained by respectively testing 24 repeats of high, medium and low concentrations and calculating according to standard deviations thereof/average value×100%.

3.2.2 Inter-batch coefficient of variation: requirement≤10%, method: the coefficient of variation was obtained by respectively testing 24 repeats of high, medium and low concentrations and calculating according to standard deviation thereof/average value×100%.

TABLE 28

Results of intra-batch and inter-batch assay
Item NO. PA1-18100037-MRJP4
Experimental Method Double-anti-sandwich method
Coating antibody 6H9, 1 μg/mL,CB, directly coating
Detection antibody 8C9-Bio, detecting at 1:3000
HRP 1:4000
Experiment reaction time 2 hours + 1 hour + 1 hour + 20 min
Experiment date 2018 Nov. 29

| Standard curve (ng/mL) | OD1 Value | OD2 Value | Mean OD | OD-background value | SD | CV % |
|---|---|---|---|---|---|---|
| 100 | 2.423 | 2.543 | 2.483 | 2.459 | 0.084923524 | 3.420 |
| 50 | 1.612 | 1.524 | 1.568 | 1.544 | 0.062225397 | 3.968 |
| 25 | 1.085 | 0.985 | 1.035 | 1.011 | 0.070710678 | 6.829 |
| 12.5 | 0.698 | 0.681 | 0.690 | 0.666 | 0.012020815 | 1.743 |
| 6.25 | 0.414 | 0.393 | 0.403 | 0.379 | 0.014919953 | 3.700 |
| 3.125 | 0.323 | 0.291 | 0.307 | 0.283 | 0.022556706 | 7.344 |
| 1.563 | 0.212 | 0.193 | 0.202 | 0.178 | 0.0127968633 | 6.322 |
| 0 | 0.152 | 0.145 | 0.149 | 0.000 | 0.005020458 | 3.375 |

3.3 Minimum Detection Limit

One-half of the concentration at the lowest end of the standard curve was generally met. Formula: A determined mean value of 20 repeats of a blank sample plus a double standard deviation.

4. Product Performance Indicators of the Kit

Detection range: 1.563 ng/mL-100 ng/mL.
Sensitivity: 3.758 ng/mL.
Precision: intra-batch CV %<8%, and inter-batch CV %<10%.
Specificity: this kit specifically detected the MRJP4 and had no cross reaction with other related proteins.
Stability results: the stability test passed.

5. Components of the Kit

TABLE 29

| Components of the kit | |
|---|---|
| Components | 96T (96 tests) |
| Assay plate | 12 strips × 8 wells |
| Standard | 2 bottles (lyophilized product) |
| Biotin-labeled Antibody (Biotin-antibody) | 1 × 120 μL/bottle (100×) |
| HRP-labeled Avidin (HRP-avidin) | 1 × 120 μL/bottle (100×) |
| Biotin-labeled Antibody Diluent (Biotin-antibody Diluent) | 1 × 15 mL/bottle |
| HRP-labeled Avidin Diluent (HRP-avidin Diluent) | 1 × 15 mL/bottle |
| Sample Diluent | 1 × 50 mL/bottle |
| Concentrated Washing Solution (Wash Buffer) | 1 × 20 mL/bottle (25×) |
| Substrate Solution (TMB Substrate) | 1 × 10 mL/bottle |
| Stop Solution | 1 × 10 mL/bottle |
| Plate labels | 4 |

6. Collection and Preservation of Sample 6.1. Serum: whole blood sample should be placed at room temperature for 2 hours or 4° C. overnight, centrifuged at 1000×g for 15 min at 2° C.-8° C., the supernatant was removed and detected immediately or the supernatant could be sub-packed to obtain specimens. The specimens should be stored at −20° C. or −80° C. and avoided from being frozen and thawed repeatedly. The thawed specimen should be centrifuged again for detecting.

6.2. Plasma: EDTA or heparin could be used as an anticoagulant. The sample was centrifuged at 1000×g for 15 min at 2° C.-8° C. within 30 min after collection. The supernatant was removed and should be detected immediately, or could be sub-packed to obtain specimens. The specimens should be stored at −20° C. or −80° C. and avoided from being frozen and thawed repeatedly. The thawed specimen should be centrifuged again for detecting.

6.3. Supernatant of cell culture: the sample was centrifuged at 1000×g for 15 min at 2° C.-8° C. The supernatant was immediately used for experimentation; or the supernatant was sub-packed, stored at −20° C. or −80° C., and avoided from being frozen and thawed repeatedly.

6.4. Urine: the urine was collected in a sterile tube at 2° C.-8° C. and centrifuged at 1000×g for 15 min. The supernatant was removed and immediately used for experimentation or was sub-packed to obtain a specimen. The specimen was stored at −20° C. or −80° C. and avoided from being frozen and thawed repeatedly. The thawed specimen should be centrifuged again before detection to remove some precipitate which occurred during the storage of the specimen.

6.5. Tissue lysate: 100 mg of tissue was selected and washed off the blood stain with 1×PBS. Then, the tissue was cut into small pieces, placed in a tissue grinder (homogenation tube), and added with 1 mL of 1×PBS to prepare a homogenate. Then, the homogenate was placed at ×20° C. overnight. After the cell membrane was destroyed by two times of repeated freezing and thawing treatment, the homogenate of the tissue was centrifuged at 5000×g for 5 min at 2° C.-8° C. and the supernatant was removed. An appropriate amount of the supernatant was immediately used for experimentation or the supernatant was sub-packed to obtain specimens and the specimens were stored at −20° C. or −80° C. The thawed specimen should be centrifuged again for detecting. Repeated freezing and thawing should be avoided.

6.6. Treatment method of Royal jelly: the sample was diluted with 3 sample volumes of PBS. An ultrasonic treatment was performed 20 times after being sufficiently shaken and then centrifuged at 10,000×g for 15 min. The supernatant was removed. Due to the high viscosity of the sample, it was recommended to dilute at 1:200 and then immediately use for experimentation or be sub-packed and stored at −20° C. or −80° C. after mixing evenly. Repeated freezing and thawing should be avoided.

Note: The hemolysis of the sample will affect the final detection results. Therefore, the hemolysis samples are not suitable for this detection.

7. Preparation of Reagents 7.1 Standard 7.1.1 One cryotube containing a standard substance was taken from a kit and centrifuged at 6000-10000 rpm for 30 s. The standard substance was dissolved with 1 mL of a sample diluent, and was sucked repeatedly 5 times to help dissolve by using a pipette with the pipette tip aligned at the bottom of the freezing tube. The standard S7 was obtained after evenly mixing and stored for subsequent use.

7.1.2 Seven 1.5 mL centrifuge tubes were selected and labeled (S0 to S6) in order, and were added with 250 μL of the sample diluent, respectively. 250 μL of the standard S7 was added into the first centrifuge tube (S6) and mixed evenly by gently sucking repeatedly. 250 μL of the solution of S6 was added into the second eppendorf (EP) tube (S5) and mixed evenly by gently sucking repeatedly. Similarly, the serial dilution of the standard was performed and S0 is the sample diluent.

TABLE 30

| | Concentrations of standards | | | | | | | |
|---|---|---|---|---|---|---|---|---|
| NO. | S7 | S6 | S5 | S4 | S3 | S2 | S1 | S0 |
| ng/mL | 100 | 50 | 25 | 12.5 | 6.25 | 3.125 | 1.5625 | 0 |

7.2 Working Solution for Washing Solution

The concentrated washing solution was diluted with deionized water at 1:25. For example, 240 mL of the deionized water was taken by a measuring cylinder, poured into a beaker or other clean container and then 10 mL of the concentrated washing solution was evenly added, stirred and mixed sufficiently. The preparation was finished before use. When the concentrated washing solution was stored at a low temperature, salt would be precipitated. The concentrated washing solution could be heated to help dissolve the salt in a water bath.

7.3 Working Solution of Biotin-Labeled Antibody

The solution of the biotin-labeled antibody was diluted with a biotin-labeled antibody diluent at 1:100. For example, 10 μL of the biotin-labeled antibody was added with 990 μL of the biotin-labeled antibody dilution and mixed gently. The preparation was finished within 10 minutes before use.

7.4 Working Solution of HRP-Labeled Avidin Diluent

HRP-labeled avidin was diluted with an HRP-labeled avidin diluent at 1:100. For example, 10 μL of HRP-labeled avidin was added with 990 μL of the HRP-labeled avidin diluent and mixed gently. The preparation was finished within 10 minutes before use.

8. A fresh royal jelly sample was subjected to a serial dilution and then detected by the enzyme-linked immunoassay kit of the present invention and the results of the data presentation are shown in Table 31.

TABLE 31

Data presentation of detection of a fresh royal jelly sample after gradient dilutio

| | light absorption value | | light absorption value | | light absorpption value | | light absorption value | | light absorption value |
|---|---|---|---|---|---|---|---|---|---|
| 150 times diluted with PBS | 2.7059 | 300 times diluted with PBS | 1.6091 | 450 times diluted with PBS | 1.3302 | 600 times diluted with PBS | 1.0482 | 750 times diluted with PBS | 0.8680 |
| 150 times diluted with PBS | 2.8036 | 300 times diluted with PBS | 1.6824 | 450 times diluted with PBS | 1.3148 | 600 times diluted with PBS | 1.1794 | 750 times diluted with PBS | 0.8694 |
| 150 times diluted with PBS | 2.9190 | 300 times diluted with PBS | 1.8174 | 450 times diluted with PBS | 1.5163 | 600 times diluted with PBS | 1.1443 | 750 times diluted with PBS | 0.9344 |
| 150 times diluted with PBS | 2.8145 | 300 times diluted with PBS | 1.7774 | 450 times diluted with PBS | 1.4568 | 600 times diluted with PBS | 1.1256 | 750 times diluted with PBS | 0.8888 |
| 150 times diluted with PBS | 2.8253 | 300 times diluted with PBS | 1.7102 | 450 times diluted with PBS | 1.4025 | 600 times diluted with PBS | 1.1554 | 750 times diluted with PBS | 0.8569 |
| Mean value | 2.8137 | | 1.7193 | | 1.4041 | | 1.1306 | | 0.8835 |
| MRJP4 concentration (mg/100 g) | 2.4 | | 2.4 | | 2.52 | | 2.52 | | 2.4 |

Figure 11:
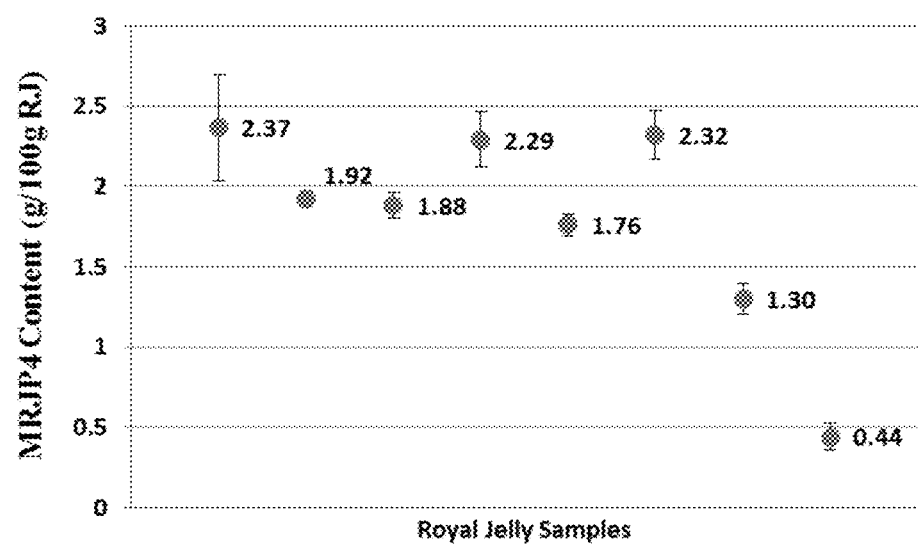
FIG. 11 shows a result of detected data of an ELISA kit for detecting MRJP4 prepared by the present invention.

FIG. 11 and Table 32 show the results of detecting the fresh royal jelly sample by the enzyme-linked immunosorbent assay kit of the present invention.

Table 32 the results of detecting the fresh royal jelly sample by the enzyme-linked immunosorbent assay kit

| | MRJP4 Content (g/100 g RJ) | | | |
|---|---|---|---|---|
| | Test 1 | Test 2 | Test 3 | Average |
| Q1 | 2.8354 | 2.1551 | 2.1154 | 2.37 |
| Q2 | 1.8513 | 1.9689 | 1.9494 | 1.92 |
| Q3 | 1.8046 | 1.9894 | 1.8529 | 1.88 |
| Q4 | 2.3952 | 2.4307 | 2.0486 | 2.29 |
| Q5 | 1.8274 | 1.6665 | 1.7881 | 1.76 |
| M1 | 2.3008 | 2.1495 | 2.5134 | 2.32 |
| M2 | 1.4322 | 1.2689 | 1.2079 | 1.30 |
| M3 | 0.3411 | 0.4417 | 0.5420 | 0.44 |

Embodiment 3 Establishment of Royal Jelly MRJP4 Colloidal Gold Immunochromatography and Development of Royal Jelly MRJP4 Colloidal Gold Immunoassay Test Strip 1. Establishment of Royal Jelly MRJP4 Colloidal Gold Immunochromatography 1.1 Optimization of Optimum pH for Antibody Labeling A mouse monoclonal antibody 1 against MRJP4 was labeled with 0.02% 20 nm colloidal gold, and the optimum pH of binding the antibody to the colloidal gold was determined by a colloidal gold gradient method. The details are as follows.

1.1.1 Nine small glass test tubes were selected and added with 1 mL of prepared colloidal gold solution respectively.

1.1.2 The pH of the colloidal gold solution was adjusted to 6.5, 7.0, 7.5, 8.0, 8.5, 9.0, 9.5 with 0.2 mol/L potassium carbonate solution, respectively.

1.1.3 The above tubes containing the colloidal gold solution were added with 50 μL of 1 mg/mL mouse monoclonal antibody 1 against the MRJP4, evenly mixed, and then placed at room temperature for 20 min.

1.1.4 Then, each of the tubes were added with 100 μL of 10% NaCl solution, evenly mix, and then stood at room temperature for 1-2 hours;

1.1.5 The change in the color of the colloidal gold was observed and a minimum pH when the color maintained red was recorded.

1.1.6 Then, the pH was adjusted to the minimum pH±0.1 in the gradient. The above test was repeated and if the recorded minimum pH at which the color still remains red, then the recorded minimum pH was regarded as the optimum pH.

Through the colloidal gold gradient method, the optimum pH of binding the mouse monoclonal antibody 1 against to the colloidal gold was determined as 7.4.

1.2 Selection of Optimal Amount of Antibody

The optimal concentration of the mouse monoclonal antibody 1 against the MRJP4 when conjugated with the colloidal gold was determined by a protein gradient method. The details are as follows.

1.2.1 Ten small glass test tubes were selected and added with 1 mL of the colloidal gold solution adjusted to the optimum pH, respectively.

1.2.2 The mouse monoclonal antibody 1 against the MRJP4 was diluted with purified water to 1 mg/mL, and 0 μL, 5 μL, 10 μL, 20 μL, 30 μL, 40 μL, 60 μL, and 80 μL of the 1 mg/mL mouse monoclonal antibody 1 against the MRJP4 were added into the above small glass test tubes in sequence and mixed evenly.

1.2.3 After being placed for 10 min, each of the small glass test tubes was added with 0.1 mL of 10% NaCl aqueous solution, mixed evenly, and stood for 1-2 hours at room temperature to observe the results.

1.2.4 Color change of the small test tubes was observed. In the control tube and the test tube added with a protein amount that was not enough to stabilize the colloidal gold, the coagulation phenomenon that the color turned from red to blue was observed. However, in the test tubes added with a protein amount that reached or exceeded the minimum amount for stability, the color remained red. An intermediate tube in which the color of the colloidal gold solution was started to turn from red to blue was found and the protein amount in the intermediate tube was the minimum protein amount needed to stabilize 1 mL of the colloidal gold. In the actual preparation work of colloidal gold probes, the amount of antibody added was usually from 120% to 130% of the minimum protein amount.

By the protein gradient method, the test results showed that the minimum antibody amount required for the mouse monoclonal antibody 1 against the MRJP4 to stabilize 1 mL of the colloidal gold was 10 μg/mL.

1.3 Preparation and Purification of Colloidal Gold Probe 20 mL of the colloidal gold solution with the optimal pH was added to the mouse monoclonal antibody 8C9 against the MRJP4 and stirred at room temperature for 30 min to prepare a colloidal gold-antibody conjugate solution. The prepared colloidal gold-antibody conjugate solution was added with 2 mL of 10% BSA (the final concentration was 0.4%) and stirred at room temperature for 10 min, or added with 0.2 mL of 10% polyethylene glycol (MW20000) and stirred at room temperature for 10 min, and then centrifuged at 9000-11000 r/min for 40-60 min. The supernatant was discarded and the precipitate was dissolved in 2 mL of a colloidal gold-antibody preservation solution and filtered through a 0.45 μm membrane filter to obtain a colloidal gold-antibody conjugate stock solution. After 1 mL of 10% aqueous NaCl solution was added to 1 mL of the colloidal gold-antibody conjugate stock solution, the solution remained a precipitate-free purple-red solution, indicating that the prepared colloidal gold-antibody conjugate stock solution had a good stability.

1.4 Determination of Working Concentration of Colloidal Gold-Antibody Conjugate Stock Solution and Preparation of Gold Colloidal Conjugate Pad The colloidal gold-antibody conjugate stock solution was diluted with a working solution at 1:2, 1:4, 1:8, and 1:16. 1.4 mL of the colloidal gold-antibody conjugate diluent and was uniformly applied to a glass fiber membrane. Then the glass fiber membrane was dried at 37° C. to obtain the gold colloidal conjugate pad. After testing, the optimum working concentration of the colloidal gold-labeled antibody was determined.

The test results showed that when the working concentration of the colloidal gold-antibody conjugate stock solution was 1:4, the obtained gold colloidal conjugate pad had the best detection effect.

1.5 Selection of Different Types of Nitrocellulose Membranes (NC membranes)

Several different types of NC membranes were selected and tested to determine the optimum type of the NC membrane through a functional test of running on plates, tests of the fluidity, hysteresis and background residue of the colloidal gold solution on different types of NC membranes and a re-selection test of NC membranes.

After the comprehensive evaluation through the function test of running on the plates, the test of chromatographic performance and the re-selection test, the type of the NC membrane was Sartorius CN140.

1.6 Establishment and Optimization of Conditions for Detection Line (T line) and Quality Control Line (C line)

The coating antibodies in the T line and C line on the NC membrane were set with several concentration gradients and the concentrations of the group with the best color development effect were selected as the use concentration (T line) and the use concentration of the goat anti-mouse IgG antibody (C line).

The results showed that, in the concentrations of the group with the best color development effect, the working concentration of the mouse monoclonal antibody 6H9 against the MRJP4 (on the T line) was 2 mg/mL and the working concentration of the goat anti-mouse IgG antibody (C line) was 1 mg/mL.

1.7 Membrane Spotting of T line and C line

The mouse monoclonal antibody 2 against the MRJP4 and the goat anti-mouse IgG antibody were each diluted to the required concentration with 0.01 mol/L PBS having a pH of 8.0 and spotted on a NC membrane by a dispenser. The distance between the T line and the C line was 0.5 cm, the parameters were all 1 µL/cm, and the sprayed NC membrane was dried at 37° C.-45° C. for more than 8 hours.

2. Assembly and Result Evaluation of the Royal Jelly MRJP4 Colloidal Gold Immunoassay Test Strip 2.1 Assembly (1) A polyvinyl chloride (PVC) bottom plate was cut into strips having a width of 2.8 mm and a length of 6 cm;

(2) An antibody solid phase NC membrane was attached in the middle of the PVC bottom plate strip, 1.5 cm from the upper section.

(3) A glass fiber membrane probe strip was attached at the lower end of the PVC bottom plate (i.e., close to the end of the T line on the NC membrane) and overlapped with the antibody solid phase NC membrane by 0.1 cm. Then, a sample pad (glass fiber membrane) having a width of 1.7 cm was attached at the lower end of the glass fiber membrane probe strip, and overlapped with the probe strip by 0.1-0.2 cm.

(4) An absorbent paper having a width of 1.7 cm was attached at the upper end of the PVC bottom plate (i.e., close to the end of the C line in the NC membrane) and overlapped with the antibody solid phase NC membrane by 0.1-0.2 cm;

(5) Test strips having a width of 2.8 mm were cut.

2.2 Result Determination

A test strip detection card was randomly selected, 60 µL, of a prepared sample to be detected was added dropwise to the sample well and reacted at room temperature for 15 min. The detection results showed, for the standard negative case, only one rose red band was presented on the C line and the standard positive case, two rose red bands were presented, wherein one was presented on the T line and the other was presented on the C line. The C line should be colored, otherwise the test strip was invalid.

2.3 Various Properties of the MRJP4 Colloidal Gold Immunoassay Test Strip

A MRJP4 targeted rapid detection card has properties of convenient, fast and sensitive, and was suitable for large-scale sample detection on site. The detection card includes an antigen immobilized in the test zone (T) on a nitrocellulose membrane, a secondary antibody immobilized in the control zone (C) on the nitrocellulose membrane, and a gold-labeled antibody immobilized on a binding pad. If a sample was positive, then one purple-red band was presented in the T zone after loading the sample. If the sample is negative, then no purple-red band was presented in the T zone. The purple-red band appeared in the C zone regardless of the presence of the MRJP4 protein in the sample.

Collection and Preservation of Sample

1. Serum: whole blood sample should be placed at room temperature for 2 hours or 4° C. overnight, centrifuged at 1000×g for 15 min at 2° C.-8° C. The supernatant was removed and detected immediately or could be sub-packed to obtain specimens. The specimens were stored at −20° C. or −80° C. and avoided from being frozen and thawed repeatedly. The thawed specimen should be centrifuged again for detecting.

2. Plasma: EDTA or heparin could be used as an anticoagulant. The sample was centrifuged at 1000×g for 15 min at 2° C.-8° C. within 30 min after collection. The supernatant was removed and detected immediately or could be sub-packed to obtain specimens. The specimens should be stored at −20° C. or −80° C. and avoided from being frozen and thawed repeatedly. The thawed specimen should be centrifuged again for detecting.

3. Cell culture supernatant: the sample was centrifuged at 1000×g for 15 min at 2° C.-8° C. The supernatant was immediately used for experimentation or was sub-packed, stored at −20° C. or −80° C., and avoided from being frozen and thawed repeatedly.

4. Urine: the urine was collected in a sterile tube at 2° C.-8° C. and centrifuged at 1000×g for 15 min. The supernatant was immediately used for experimentation or was sub-packed to obtain specimens. The specimens were stored at −20° C. or −80° C. and avoided from being frozen and thawed repeatedly. The thawed specimen should be centrifuged again before being detected to remove some precipitate which occurred during the storage of the specimen.

5. Animal tissue lysate: 100 mg of tissue was selected and washed off the blood stain with 1×PBS. Then, the tissue was cut into small pieces, placed in a tissue grinder (homogenation tube), and added with 1 mL of 1×PBS to prepare a homogenate. Then, the homogenate was placed at −20° C. overnight. After the cell membrane was destroyed by two times of repeated freezing and thawing treatment, the homogenate of the tissue was centrifuged at 5000×g for 5 min at 2° C.-8° C., and the supernatant was removed. An appropriate amount of the supernatant was immediately used for experimentation or the supernatant was sub-packed to obtain specimens and the specimens were stored at −20° C. or −80° C. The thawed specimen should be centrifuged again for detecting. Repeated freezing and thawing should be avoided.

6. Plant tissue lysate: about 0.5 g of the washed plant tissue (dried with filter paper) was weighted, cut into pieces with sterile scissors and then added to a pre-cooled mortar after sterilization and ground into powder with liquid nitrogen. The powder (about 0.5 mL of powder) was collected into a labeled corresponding 2 mL EP tube, 1 mL of plant tissue extract containing a protease inhibitor mixture (added before use) and mixed by gently sucking using a pipette with the pipette tip to obtain a mixture. The mixture stood in an ice bath for 20 min and vortexed every 10 min; followed by ultrasonic treatment for 5 min, at a power of 20%. Then, centrifugation was carried out at 12,000 r/min for 4 min at 4° C. and the supernatant was removed as the total protein. Note: hemolysis of the sample will affect the final detection results. Therefore, the hemolysis samples are not suitable for this detection.

Detection Steps

1. The sample was taken from the −80° C. refrigerator and thawed for detecting.

2. A detection card was taken out and put on a table after opening. A dropper coming with this product was applied to absorb the supernatant of the sample to be detected and 3 drops were add into the sample well.

3. 5-10 minutes after adding the sample, the color development zone was observed to determine the result.

Figure 12:
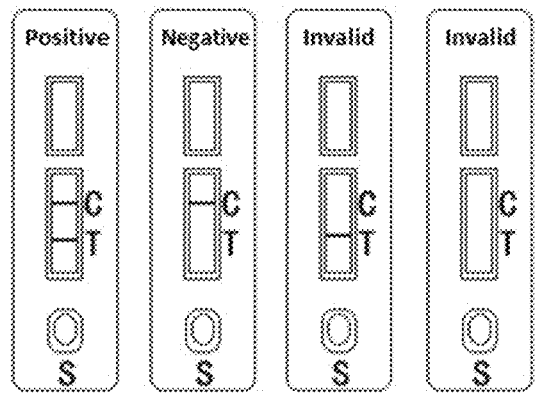
FIG. 12 shows a judgment standard of a test result of a colloidal gold immunoassay test strip for detecting MRJP4 prepared by the present invention.

4. Result determination: referring to FIG. 12.

Positive: if a color was presented in the C line and a naked-eye visible color was presented in the T line, then this case was determined to be positive regardless of the color depth. Negative: if a color was presented in the C line and no naked-eye visible color was presented in the T line, then this case was determined to be negative. Invalid: if no color was presented in the C line regardless of whether a color was presented in the T line or not, then the detection card was determined to be invalid.

Figure 13:
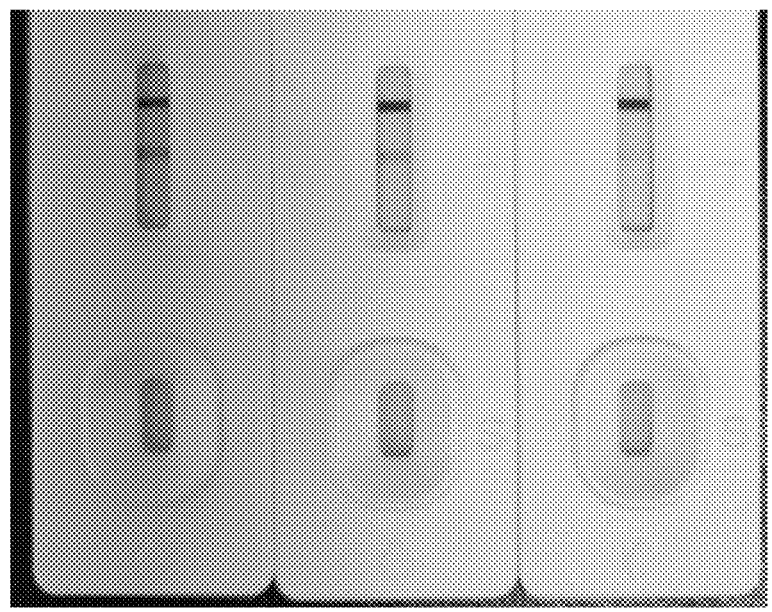
FIG. 13 shows a result of detected data of a colloidal gold immunoassay test strip for detecting MRJP4 prepared by the present invention.

FIG. 13 shows a result of a sample detected by the colloidal gold detection card prepared by the present invention.

Test Example 1 Specificity Test of Royal Jelly MRJP4 Detected by Colloidal Gold Test Strip of the Present Invention A fresh royal jelly sample was diluted with a phosphate buffer solution to replace the royal jelly sample for measuring the specificity of the test strip. The results showed that: PBS and sample diluent showed only one rose red band presented in the C line. The royal jelly sample showed two rose red bands separately presented in the T line and the C line, indicating that the royal jelly MRJP4 colloidal gold test strip only reacted specifically with the MRJP4 and had no cross reaction with other related proteins (A family of major royal jelly proteins consists of proteins 1-9 and the contents of proteins 1-5 are the highest, accounting for 82%-90% of that of the major royal jelly proteins).

Test Example 2 Sensitivity Test of Detecting Royal Jelly MRJP4 by the Enzyme-Linked Immunosorbent Assay Kit of the Present Invention The detection results showed that the sensitivity of the kit of the present invention for detecting the royal jelly MRJP4 was 3.758 ng/mL.

Test Example 3 Thermal Damage Test of the Enzyme-Linked Immunosorbent Assay Kit of the Present Invention Determination results: the test and reduction rate of the sample: the concentration determined value of the sample (stored at −80° C.) was 1260 ng/mL. After being damaged at 4° C./−20° C./room temperature, the reduction rates of the samples were close to each other and the reduction rate ranged from 30% to 50%.

TABLE 33

Results of Thermal Damage Test of the Kit

| Standard curve (ng/mL) | OD value-0 day | OD value-4$^{th}$ day | OD value-7$^{th}$ day | Reduction rate |
|---|---|---|---|---|
| 100 | 2.872 | 2.6978 | 2.1478 | 25% |
| 50 | 1.9835 | 1.745 | 1.5274 | 23% |
| 25 | 1.271 | 1.0524 | 0.9702 | 24% |
| 12.5 | 0.7655 | 0.6855 | 0.6917 | 10% |
| 6.25 | 0.4689 | 0.4125 | 0.4834 | −3% |
| 3.125 | 0.3235 | 0.2997 | 0.2635 | 19% |
| 1.563 | 0.2388 | 0.2451 | 0.2374 | 1% |
| 0 | 0.1635 | 0.1722 | 0.1814 | −11% |

The test results showed that the thermal stabilities in 7 days were all reduced by less than 30% and the thermal stabilities were qualified. Next, an intra-batch and an inter-batch assay were performed to evaluate the reproducibility of the kit.

Test Example 4 Reproducibility Test of the Enzyme-Linked Immunosorbent Assay Kit of the Present Invention for Detecting the Royal Jelly MRJP4

Figure 14:
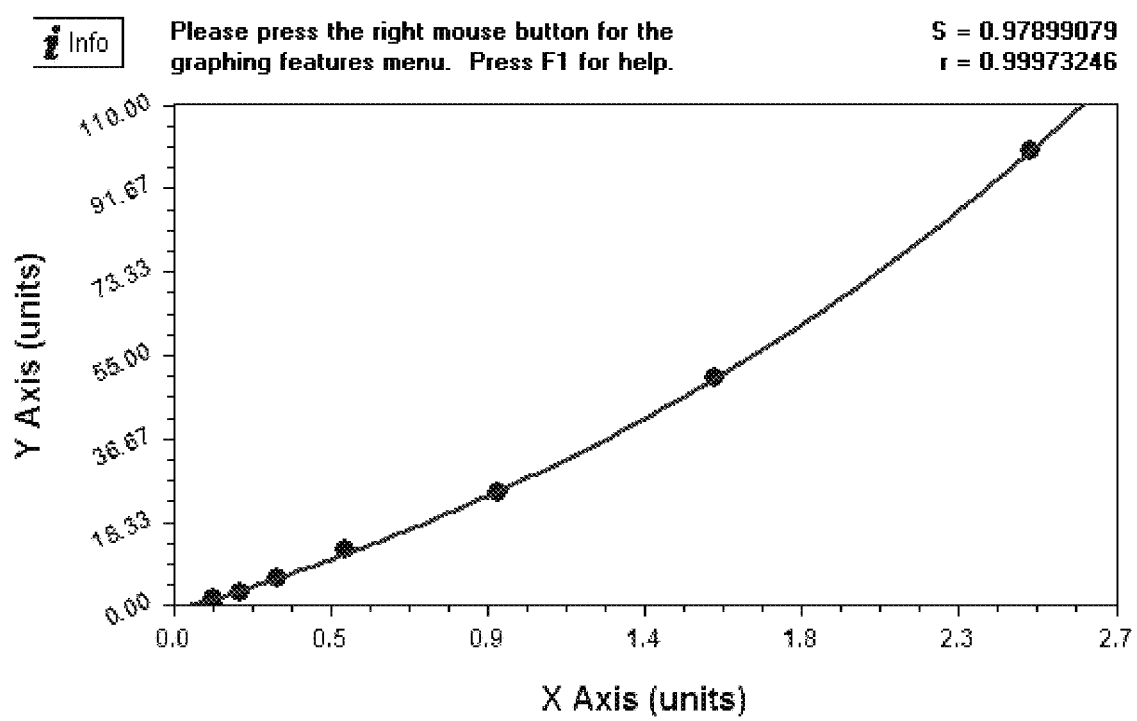
FIG. 14 shows results an intra-assay and inter-assay variation of an ELISA kit for detecting MRJP4 prepared by the present invention.

Five royal jelly samples from different batches and five samples from the same batch were detected by the enzyme-linked immunosorbent assay kit of the present invention and each sample was repeatedly tested 10 times. The detection results were completely consistent and the trend of the detection results between different batches and within the same batch was consistent (FIG. 14), which met the expectations.

TABLE 34

Results of reproducibility test of the kit

| Standard curve (ng/mL) | OD1 value | OD2 value | Mean OD | OD-background value | SD (Standard deviation) | CV % |
|---|---|---|---|---|---|---|
| 100 | 2.423 | 2.543 | 2.483 | 2.459 | 0.084923524 | 3.420 |
| 50 | 1.612 | 1.524 | 1.568 | 1.544 | 0.062225397 | 3.968 |
| 25 | 1.085 | 0.985 | 1.035 | 1.011 | 0.070710678 | 6.829 |
| 12.5 | 0.698 | 0.681 | 0.690 | 0.666 | 0.012020815 | 1.743 |
| 6.25 | 0.414 | 0.393 | 0.403 | 0.379 | 0.014919953 | 3.700 |
| 3.125 | 0.323 | 0.291 | 0.307 | 0.283 | 0.022556706 | 7.344 |
| 1.563 | 0.212 | 0.193 | 0.202 | 0.178 | 0.012798633 | 6.322 |
| 0 | 0.152 | 0.145 | 0.149 | 0.000 | 0.005020458 | 3.375 |

What is claimed is:

1. A hybridoma cell line 6H9 stably secreting a monoclonal antibody against a major royal jelly protein 4 (MRJP4), having a microbial deposit number of CGMCC No. 17294.

2. A monoclonal antibody against the MRJP4, secreted by the hybridoma cell line 6H9 of claim 1.

3. A hybridoma cell line 8C9 stably secreting a monoclonal antibody against MRJP4, having a microbial deposit number of CGMCC No. 17295.

4. A monoclonal antibody against the MRJP4, secreted by the hybridoma cell line 8C9 of claim 3.

5. A method of detecting MRJP4 in a sample, comprising the following step: applying the monoclonal antibody against the MRJP4 of claim 2 for qualitatively detecting whether the sample contains MRJP4 or for quantitatively detecting a content of the MRJP4 in the sample.

6. An enzyme-linked immunosorbent assay kit for detecting a content of MRJP4, comprising: a primary antibody against the MRJP4, a biotin-labeled secondary antibody against the MRJP4, a standard, a horseradish peroxidase-labeled avidin, a biotin-labeled antibody diluent, a horseradish peroxidase-labeled avidin diluent, a sample diluent, a concentrated washing solution, a substrate solution, and a stop solution; wherein
the primary antibody is a first monoclonal antibody against the MRJP4 and the biotin-labeled secondary antibody is a second monoclonal antibody against the MRJP4; or the primary antibody is the second monoclonal antibody against the MRJP4 and the biotin-labeled secondary antibody is the first monoclonal antibody against the MRJP4;
wherein the first monoclonal antibody against the MRJP4 is secreted by a hybridoma cell line 6H9 having a microbial deposit number of CGMCC No. 17294 and the second monoclonal antibody against the MRJP4 is secreted by a hybridoma cell line 8C9 having a microbial deposit number of CGMCC No. 17295.

7. A colloidal gold immunoassay test strip for detecting MRJP4, comprising: a gold colloidal conjugate pad, a nitrocellulose (NC) membrane containing a detecting line and a quality controlling line, a sample pad, a water absorbing pad, and a detecting bottom plate; wherein,
the gold colloidal conjugate pad comprises a conjugate of a first monoclonal antibody and a colloidal gold; the NC membrane comprises one detecting line and one quality controlling line; the detecting line is composed of a second monoclonal antibody, and the quality controlling line is composed of a goat anti-mouse immunoglobulin G (IgG) antibody; or
the gold colloidal conjugate pad comprises a conjugate of the second monoclonal antibody and a colloidal gold; the NC membrane comprises one detecting line and one quality controlling line; the detecting line is composed of the first monoclonal antibody, and the quality controlling line is composed of a goat anti-mouse immunoglobulin G (IgG) antibody;
wherein the first monoclonal antibody is secreted by a hybridoma cell line 6H9 having a microbial deposit number of CGMCC No. 17294 and the second monoclonal antibody is secreted by a hybridoma cell line 8C9 having a microbial deposit number of CGMCC No. 17295.

8. A method for preparing the gold colloidal conjugate pad of the colloidal gold immunoassay test strip of claim 7, comprising the following steps:
(1) conjugating a colloidal gold solution with a monoclonal antibody secreted by the hybridoma cell line 6H9 having the microbial deposit number of CGMCC No. 17294 or a monoclonal antibody secreted by the hybridoma cell line 8C9 having the microbial deposit number of CGMCC No. 17295 to obtain a colloidal gold-antibody conjugate stock solution; and
(2) diluting the colloidal gold-antibody conjugate stock solution and then uniformly adding onto a glass fiber membrane and performing drying to obtain the gold colloidal conjugate pad.

9. The method for preparing the gold colloidal conjugate pad of the colloidal gold immunoassay test strip of claim 8, wherein, in the step (1), the monoclonal antibody secreted by the hybridoma cell line 6H9 having the microbial deposit number of CGMCC No. 17294 or secreted by the hybridoma cell line 8C9 having the microbial deposit number of CGMCC No. 17295 is conjugated with the colloidal gold solution at a pH of 7.4; and in the step (2), the colloidal gold-antibody conjugate stock solution is diluted with a working solution at a volume ratio of 1:4 and uniformly added onto the glass fiber membrane.

10. The colloidal gold immunoassay test strip of claim 7, wherein, a working concentration of the monoclonal antibody secreted by the hybridoma cell line 6H9 having the microbial deposit number of CGMCC No. 17294 or secreted by the hybridoma cell line 8C9 having the microbial deposit number of CGMCC No. 17295 on the detecting line is 2 mg/mL, and a working concentration of the goat anti-mouse IgG antibody on the quality controlling line is 1 mg/mL.

11. A method of detecting MRJP4 in a sample, comprising the following step: applying the monoclonal antibody against the MRJP4 of claim 4 for qualitatively detecting whether the sample contains MRJP4 or for quantitatively detecting a content of the MRJP4 in the sample.

* * * * *

SEQUENCE LISTING

<160> NUMBER OF SEQ ID NOS: 1

<210> SEQ ID NO 1
<211> LENGTH: 333
<212> TYPE: PRT
<213> ORGANISM: Artificial Sequence
<220> FEATURE:
<223> OTHER INFORMATION: The sequence is synthesized.

<400> SEQUENCE: 1

```
Ile Ala Ile Asp Glu Tyr Glu Arg Leu Trp Val Leu Asp Ser Gly Leu
1               5                   10                  15

Val Asn Asn Thr Gln Pro Met Cys Ser Pro Lys Leu Phe Ala Phe Asp
            20                  25                  30

Leu Asn Thr Ser Gln Leu Leu Lys Gln Val Glu Ile Pro His Asp Val
        35                  40                  45

Ala Thr Thr Gly Lys Gly Glu Leu Val Ser Leu Thr Val Gln Ala Met
    50                  55                  60

Asp Ser Thr Asn Thr Met Val Tyr Met Val Asp Asn Lys Asn Thr Leu
65                  70                  75                  80

Ile Ile Tyr Gln Asn Ala Asp Asp Ser Phe His Arg Leu Ser Ser His
                85                  90                  95

Thr Leu Asn His Asn Ser Asp Lys Met Ser Asp Gln Gln Glu Asn Leu
            100                 105                 110

Thr Leu Lys Glu Val Asp Asn Lys Val Tyr Gly Met Ala Leu Ser Pro
        115                 120                 125

Val Thr His Asn Leu Tyr Tyr Asn Ser Pro Ser Glu Asn Leu Tyr
    130                 135                 140

Tyr Val Asn Thr Glu Ser Leu Met Lys Ser Glu Asn Gln Gly Asn Asp
145                 150                 155                 160

Val Gln Tyr Glu Arg Val Gln Asp Val Phe Asp Ser Gln Leu Thr Val
                165                 170                 175

Lys Ala Val Ser Lys Asn Gly Val Leu Leu Phe Gly Leu Ala Asn Asn
            180                 185                 190

Thr Leu Ser Cys Trp Asn Glu His Gln Ser Leu Asp Arg Gln Asn Ile
        195                 200                 205

Asp Val Val Ala Arg Asn Glu Asp Thr Leu Gln Met Val Val Ser Met
    210                 215                 220

Lys Ile Lys Gln Asn Val Pro Gln Ser Gly Arg Val Asn Asn Thr Gln
225                 230                 235                 240

Arg Asn Glu Tyr Leu Leu Ala Leu Ser Asp Arg Asn Gln Asn Val Leu
                245                 250                 255

Asn Asn Asp Leu Asn Leu Glu His Val Asn Phe Gln Ile Leu Gly Ala
            260                 265                 270

Asn Val Asn Asp Leu Ile Arg Asn Ser Arg Cys Ala Asn Phe Asp Asn
        275                 280                 285

Gln Asp Asn Asn His Tyr Asn His Asn His Asn Gln Ala Arg His Ser
    290                 295                 300

Ser Lys Ser Asp Asn Gln Asn Asn Gln His Asn Asp Gln Ala His
305                 310                 315                 320

His Ser Ser Lys Ser Asn Asn Arg His Asn Asn Asn Asp
                325                 330
```